(12) United States Patent
Townsend et al.

(10) Patent No.: US 7,955,399 B2
(45) Date of Patent: Jun. 7, 2011

(54) PROSTHETIC FOOT WITH TUNABLE PERFORMANCE

(75) Inventors: Barry W. Townsend, Bakersfield, CA (US); Byron K. Claudino, Bakersfield, CA (US)

(73) Assignee: Bioquest Prosthetics, LLC, Bakersfield, CA (US)

( * ) Notice: Subject to any disclaimer, the term of this patent is extended or adjusted under 35 U.S.C. 154(b) by 1169 days.

(21) Appl. No.: 10/594,797

(22) PCT Filed: Apr. 1, 2005

(86) PCT No.: PCT/US2005/011304
§ 371 (c)(1),
(2), (4) Date: Sep. 29, 2006

(87) PCT Pub. No.: WO2005/097011
PCT Pub. Date: Oct. 20, 2005

(65) Prior Publication Data
US 2007/0219643 A1    Sep. 20, 2007

Related U.S. Application Data

(63) Continuation-in-part of application No. 10/473,682, filed on Sep. 30, 2003, now Pat. No. 7,507,259.

(60) Provisional application No. 60/558,119, filed on Apr. 1, 2004.

(51) Int. Cl.
*A61F 2/66* (2006.01)
(52) U.S. Cl. ............................... 623/55; 623/47; 623/52
(58) Field of Classification Search .............. 623/47–55
See application file for complete search history.

(56) References Cited

U.S. PATENT DOCUMENTS

| 640,540 A | 1/1900 | Daniels |
| 810,180 A | 1/1906 | Wintermute |
| 2,453,969 A | 11/1948 | Carter |
| 3,335,428 A | 8/1967 | Gajdos |
| 4,555,817 A | 12/1985 | McKendrick |
| 4,645,509 A | 2/1987 | Poggi et al. ............. 623/55 |
| 4,721,510 A | 1/1988 | Cooper et al. |

(Continued)

FOREIGN PATENT DOCUMENTS

CA       2103341 A1      4/1995

(Continued)

OTHER PUBLICATIONS

Supplementary European Search Report dated Jan. 4, 2010; Application No. EP 05 73 3122; 4 pages.

(Continued)

*Primary Examiner* — David H Willse
*Assistant Examiner* — Javier G Blanco
(74) *Attorney, Agent, or Firm* — Antonelli, Terry, Stout & Kraus, LLP.

(57) ABSTRACT

A prosthetic foot (100) incorporates a foot keel (101) and a resilient calf shank (105) with its lower end connection to the foot keel to form an ankle joint of the prosthetic foot. The foot keel has forefoot and hindfoot portions and a midfoot portion extending between the forefoot and hindfoot portions. The calf shank extends upward from the foot keel by way of an anterior facing convexly curved portion (106) of the shank, and is secured to the foot keel by way of a coupling element (107) which is monolithically formed with the forefoot portion of the foot. The lower end of the shank is reversely curved (110) and housed by a reversely curved portion (112) of the coupling element.

6 Claims, 19 Drawing Sheets

U.S. PATENT DOCUMENTS

| | | | | |
|---|---|---|---|---|
| 4,822,363 | A | 4/1989 | Phillips | |
| 4,892,554 | A | 1/1990 | Robinson | |
| 4,911,724 | A | 3/1990 | Fikes | |
| 4,938,776 | A | 7/1990 | Masinter | |
| 4,959,073 | A | 9/1990 | Merlette | |
| 4,994,086 | A | 2/1991 | Edwards | |
| 5,019,109 | A | 5/1991 | Voisin | |
| 5,062,859 | A | 11/1991 | Naeder | |
| 5,066,305 | A | 11/1991 | Firth | |
| 5,112,356 | A | 5/1992 | Harris et al. | 623/49 |
| 5,116,383 | A | 5/1992 | Shorter et al. | |
| 5,139,525 | A | 8/1992 | Kristinsson | |
| 5,156,632 | A | 10/1992 | Wellershaus | |
| 5,181,932 | A | 1/1993 | Phillips | |
| 5,181,933 | A | 1/1993 | Phillips | |
| 5,219,365 | A | 6/1993 | Sabolich | |
| 5,258,039 | A | 11/1993 | Goh et al. | |
| 5,290,319 | A | 3/1994 | Phillips | |
| 5,312,669 | A | 5/1994 | Bedard | |
| 5,314,499 | A | 5/1994 | Collier, Jr. | 623/47 |
| 5,376,133 | A | 12/1994 | Gramnas | |
| 5,376,139 | A | 12/1994 | Pitkin | |
| 5,376,141 | A | 12/1994 | Phillips | |
| 5,387,246 | A | 2/1995 | Phillips | |
| 5,443,522 | A | 8/1995 | Hiemisch | |
| 5,443,527 | A | 8/1995 | Wilson | |
| 5,458,656 | A | 10/1995 | Phillips | |
| 5,482,513 | A | 1/1996 | Wilson | |
| 5,486,209 | A | 1/1996 | Phillips | |
| 5,507,838 | A | 4/1996 | Chen | |
| 5,509,936 | A | 4/1996 | Rappoport et al. | |
| 5,509,937 | A | 4/1996 | Allard et al. | |
| 5,509,938 | A | 4/1996 | Phillips | |
| 5,514,185 | A | 5/1996 | Phillips | |
| 5,545,230 | A | 8/1996 | Kinsinger et al. | |
| 5,549,714 | A | 8/1996 | Phillips | |
| 5,571,213 | A | 11/1996 | Allen | |
| 5,593,456 | A | 1/1997 | Merlette | |
| 5,593,457 | A | 1/1997 | Phillips | |
| 5,653,767 | A | 8/1997 | Allen et al. | |
| 5,653,768 | A | 8/1997 | Kania | |
| 5,695,526 | A | 12/1997 | Wilson | |
| 5,695,527 | A | 12/1997 | Allen | |
| 5,702,488 | A | 12/1997 | Wood et al. | |
| 5,725,598 | A | 3/1998 | Phillips | |
| 5,728,176 | A | 3/1998 | Phillips | |
| 5,728,177 | A | 3/1998 | Phillips | |
| 5,746,773 | A | 5/1998 | Littig | |
| 5,766,264 | A | 6/1998 | Lundt | |
| 5,776,205 | A | 7/1998 | Phillips | |
| 5,800,568 | A | 9/1998 | Atkinson et al. | |
| 5,800,569 | A | 9/1998 | Phillips | |
| 5,824,112 | A | 10/1998 | Phillips | |
| 5,897,594 | A | 4/1999 | Martin et al. | |
| 5,899,944 | A | 5/1999 | Phillips | |
| 5,944,760 | A | 8/1999 | Christensen | |
| 5,976,191 | A | 11/1999 | Phillips | |
| 5,993,488 | A | 11/1999 | Phillips | |
| 6,051,026 | A | 4/2000 | Biedermann et al. | 623/38 |
| 6,071,313 | A | 6/2000 | Phillips | |
| 6,077,301 | A | 6/2000 | Pusch | |
| 6,083,265 | A | 7/2000 | Shorter et al. | |
| 6,099,572 | A | 8/2000 | Mosler et al. | |
| 6,165,227 | A | 12/2000 | Phillips | |
| 6,187,052 | B1 | 2/2001 | Molino et al. | |
| 6,197,066 | B1 | 3/2001 | Gabourie | |
| 6,206,932 | B1 | 3/2001 | Johnson | |
| 6,206,934 | B1 | 3/2001 | Phillips | |
| 6,228,043 | B1 | 5/2001 | Townsend et al. | |
| 6,241,776 | B1 | 6/2001 | Christensen | |
| 6,270,468 | B1 | 8/2001 | Townsend et al. | |
| 6,280,479 | B1 | 8/2001 | Phillips | |
| 6,290,730 | B1 | 9/2001 | Pitkin et al. | |
| 6,350,286 | B1 | 2/2002 | Atkinson et al. | |
| 6,402,790 | B1 | 6/2002 | Celebi | |
| 6,406,500 | B1 | 6/2002 | Phillips | |
| 6,443,995 | B1 | 9/2002 | Townsend et al. | |
| 6,514,293 | B1 | 2/2003 | Jang et al. | |
| 6,527,811 | B1 | 3/2003 | Phillips | |
| 6,562,075 | B2 | 5/2003 | Townsend et al. | |
| 6,602,295 | B1 | 8/2003 | Doddroe et al. | |
| 6,663,673 | B2 | 12/2003 | Christensen | |
| 2002/0040249 | A1 | 4/2002 | Phillips | |
| 2002/0077706 | A1 | 6/2002 | Phillips | |
| 2002/0087216 | A1 | 7/2002 | Atkinson et al. | |
| 2002/0116072 | A1 | 8/2002 | Rubie et al. | |
| 2002/0120349 | A1 | 8/2002 | Phillips | |
| 2002/0133237 | A1 | 9/2002 | Christesen | |
| 2003/0009238 | A1 | 1/2003 | Whayne | |
| 2003/0028256 | A1 | 2/2003 | Townsend et al. | |
| 2003/0045944 | A1 | 3/2003 | Mosler et al. | |
| 2003/0093158 | A1 | 5/2003 | Phillips et al. | |
| 2003/0120354 | A1 | 6/2003 | Doddroe et al. | |
| 2003/0191540 | A1 | 10/2003 | Townsend et al. | |
| 2003/0216815 | A1 | 11/2003 | Christensen | |

FOREIGN PATENT DOCUMENTS

| | | |
|---|---|---|
| DE | 325171 C1 | 10/1920 |
| DE | 19717298 C1 | 5/1998 |
| DE | 298 20 904 U1 | 6/1999 |
| DE | 298 23 435 U1 | 9/1999 |
| DE | 29920434 U1 | 5/2002 |
| DK | 0 648 479 A1 | 10/1993 |
| EP | 0 331 468 | 9/1989 |
| EP | 0 648 479 A1 | 4/1995 |
| EP | 0793949 A1 | 9/1997 |
| FR | 2 640 499 A1 | 6/1990 |
| FR | 2 734 151 | 11/1996 |
| FR | 2734151 | 11/1996 |
| GB | 2 173 569 | 10/1986 |
| JP | 9-327473 | 12/1997 |
| JP | 11-299815 | 11/1999 |
| WO | WO 91/00070 | 1/1991 |
| WO | WO 9410942 A1 | 5/1994 |
| WO | WO 97/17042 | 5/1997 |
| WO | WO 00/71061 A1 | 11/2000 |
| WO | WO 02/02034 A1 | 1/2002 |
| WO | WO 02/30340 | 4/2002 |
| WO | WO 02/078578 A1 | 10/2002 |
| WO | WO 2004/028416 A1 | 4/2004 |

OTHER PUBLICATIONS

Japanese Office Action and translation-in-part dated Dec. 15, 2009; Application No. 506343/2007; 13 pages.

Russian Office Action; Patent Application No. 2006138501/14(041949); pp. 1-3 and English translation of the Russian Office Action pp. 1-3.

Canadian Office Action dated Feb. 16, 2009; Application No. 2,446,768; 3 pages; Owner: Barry W. Townsend, et al.; Title: Prosthetic Foot With Tunable Performance.

European Office Action dated Apr. 3, 2009; Application No. 02 733 905.0-2310; 4 pages; Applicant: Barry W. Townsend, et al.

Supplementary Partial European Search Report; EP 02 75 7836; Date : Mar. 7, 2006.

Supplementary Partial European Search Report; EP 02 71 3785; Date : Mar. 7, 2006.

International Search Report; PCT/US05/34037; Filing Date: Sep. 26, 2005.

International Search Report (Jul. 1998); International application No. PCT/US01/48954.

International Search Report (Jul. 1998); International application No. PCT/US02/09589.

International Search Report (Apr. 2002); International application No. PCT/US02/09573.

International Search Report (Apr. 2002); International application No. PCT/US02/09571.

International Search Report (Jul. 1998); International application No. PCT/US02/30471.

PCT Written Opinion from International Application No. PCT/US02/06901.

Supplementary European Search Report; EP 02 71 3785; May 22, 2006.
Supplementary European Search Report; EP 02 75 7836; May 25, 2006.
International Search Report; PCT/US03/09506; filed Mar. 31, 2003.
Universal Offset Pyramid Adapters; 2 pages.
International Search Report; PCT/US05/11304; Filing Date: Apr. 1, 2005.
International Search Report; PCT/US05/11291; Filing Date: Apr. 1, 2005.
International Search Report dated Jul. 30, 2002, from International Application No. PCT/US02/06901.
Atkinson et al.; Publ. No. US 2002/0087216 A1.
Japanese Office Action dated Jul. 21, 2009; Application No. 2007-506343; 5 pages and Translation-in-part of Japanese Office Action—5 pages.

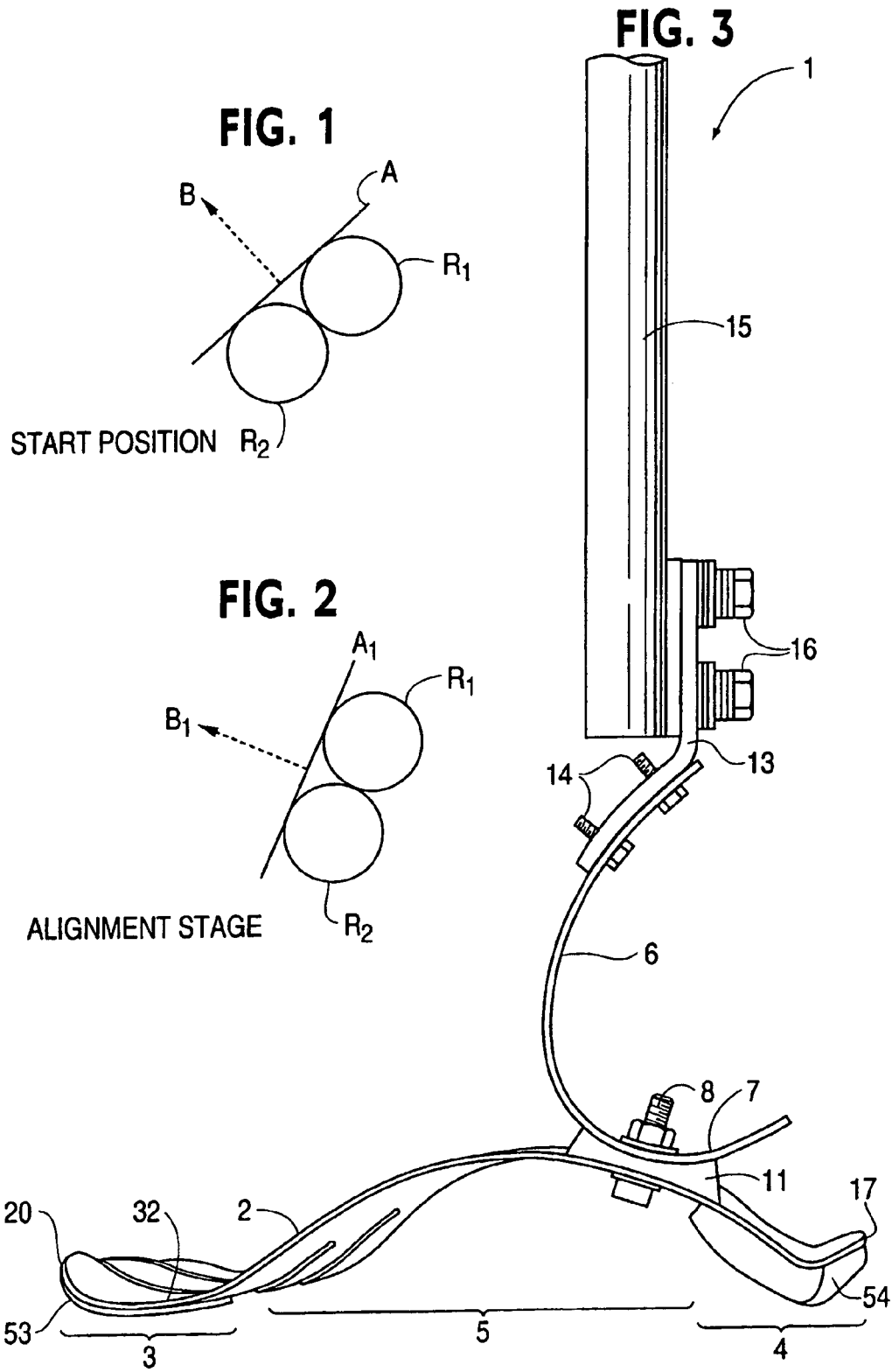

46

47

48

49

50

51

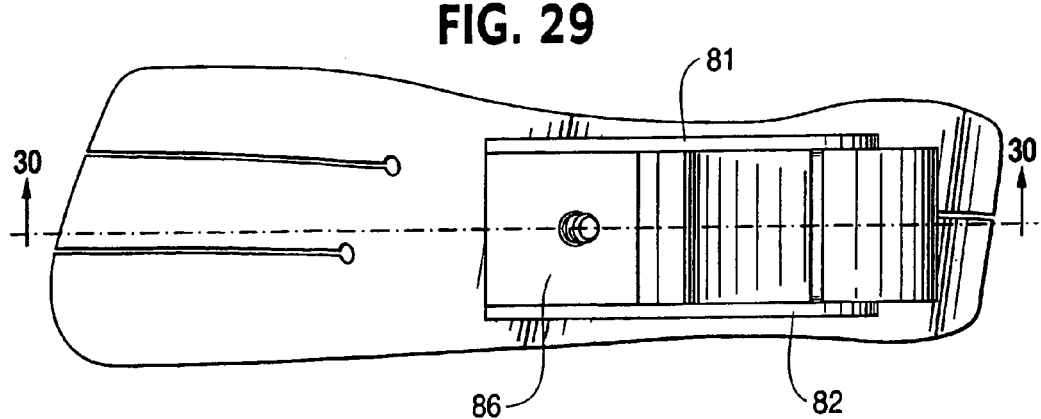
FIG. 29
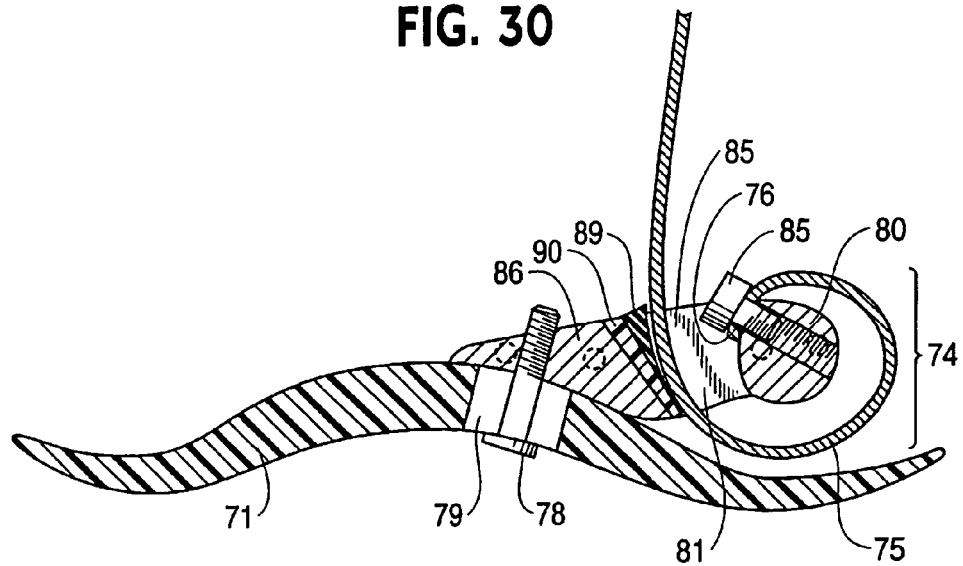
FIG. 30
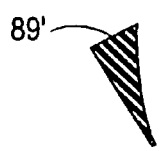  
FIG. 31A    FIG. 31B

PROSTHETIC FOOT WITH TUNABLE PERFORMANCE

RELATED APPLICATIONS

This application is a U.S. national phase of international application no. PCT/US2005/011304 filed Apr. 1, 2005 which claims priority of U.S. application Ser. No. 10/814,260 filed Apr. 1, 2004, now U.S. Pat. No. 7,611,543 issued Nov. 3, 2009, and U.S. application Ser. No. 60/558,119 filed Apr. 1, 2004, and U.S. application Ser. No. 10/814,155 filed Apr. 1, 2004, now U.S. Pat. No. 7,410,503 issued Aug. 12, 2008. This application is also a continuation in part of U.S. application Ser. No. 10/473,682 filed Sep. 30, 2003, now U.S. Pat. No. 7,507,259 issued Mar. 24, 2009.

TECHNICAL FIELD

The present invention relates to a high performance prosthetic foot providing improved dynamic response capabilities as these capabilities relate to applied force mechanics.

BACKGROUND ART

A jointless artificial foot for a leg prosthesis is disclosed by Martin et al. in U.S. Pat. No. 5,897,594. Unlike earlier solutions wherein the artificial foot has a rigid construction provided with a joint in order to imitate the function of the ankle, the jointless artificial foot of Martin et al. employs a resilient foot insert which is arranged inside a foot molding. The insert is of approximately C-shaped design in longitudinal section, with the opening to the rear, and takes up the prosthesis load with its upper C-limb and via its lower C-limb transmits that load to a leaf spring connected thereto. The leaf spring as seen from the underside is of convex design and extends approximately parallel to the sole region, forward beyond the foot insert into the foot-tip region. The Martin et al. invention is based on the object of improving the jointless artificial foot with regard to damping the impact of the heel, the elasticity, the heel-to-toe walking and the lateral stability, in order thus to permit the wearer to walk in a natural manner, the intention being to allow the wearer both to walk normally and also to carry out physical exercise and to play sports. However, the dynamic response characteristics of this known artificial foot are limited and do not mimic the human biomechanical function of the human foot, ankle and shank and soft supporting tissue. The artificial foot of Martin et al. and other prior art prosthetic feet that utilize this ankle design and a rigid pylon as a shank cannot store enough elastic energy to create normal ankle joint sagittal plane kinetic power in gait. Tests have shown that prior art prosthetic feet with such designs produce only about 25% of normal ankle joint sagittal plane kinetic power in gait.

Other prosthetic feet have been proposed by Van L. Phillips which allegedly provide an amputee with an agility and mobility to engage in a wide variety of activities which were precluded in the past because of the structural limitations and corresponding performances of prior art prostheses. Running, jumping and other activities are allegedly sustained by these known feet which, reportedly, may be utilized in the same manner as the normal foot of the wearer. See U.S. Pat. Nos. 6,071,313; 5,993,488; 5,899,944; 5,800,569; 5,800,568; 5,728,177; 5,728,176; 5,824,112; 5,593,457 5,514,185; 5,181,932; and 4,822,363, for example. These prostheses have a foot, ankle and shank made of composite material with the mechanical form of the ankle being posterior facing, convexly-curved. Tests have shown that prior art prostheses with this design produce approximately 40% of normal human ankle joint sagittal plane kinetic power in gait. There is a need for a higher performance prosthesis which can improve amputee performance in activities such as walking, running, jumping, sprinting, starting, stopping and cutting.

DISCLOSURE OF INVENTION

In order to allow the amputee to attain a higher level of performance and function, there is a need for a high performance prosthetic foot having improved applied mechanics, which foot can out perform the human foot and also out perform the prior art prosthetic feet. It is of interest to the amputee to have a high performance prosthetic foot having improved applied mechanics, high low dynamic response, and alignment adjustability that can be fine tuned to improve the horizontal and vertical components of activities which can be task specific in nature.

The prosthetic foot of the present invention addresses these needs. According to an example embodiment disclosed herein, the prosthetic foot of the invention comprises a longitudinally extending foot keel having a forefoot portion at one end, a hindfoot portion at an opposite end and a relatively long midfoot portion extending between and upwardly arched from the forefoot and hindfoot portions. A calf shank including a downward convexly curved lower end is also provided. An adjustable fastening arrangement attaches the curved lower end of the calf shank to the upwardly arched midfoot portion of the foot keel to form an ankle joint area of the prosthetic foot. The calf shank is a resilient member which forms an ankle and a shank of the prosthesis, the resilient member extending upward from the foot keel by way of an anterior facing convexly curved portion of the member. Advantageously, with this mechanical form orientation, the mechanical form's angular velocity increases in response to compressing force in late mid-stance loading. As a consequence, ankle joint sagittal plane kinetic power of the prosthesis in gait is improved.

The adjustable fastening arrangement permits adjustment of the alignment of the calf shank and the foot keel with respect to one another in the longitudinal direction of the foot keel for tuning the performance of the prosthetic foot. By adjusting the alignment of the opposed upwardly arched midfoot portion of the foot keel and the downward convexly curved lower end of the calf shank with respect to one another in the longitudinal direction of the foot keel, the dynamic response characteristics and motion outcomes of the foot are changed to be task specific in relation to the needed/desired horizontal and vertical linear velocities. A multi-use prosthetic foot is disclosed having high and low dynamic response capabilities, as well as biplanar motion characteristics, which improve the functional outcomes of amputees participating in activities of daily living, sporting and/or recreational activities. A prosthetic foot especially for sprinting is also disclosed.

The calf shank in several embodiments has its lower end reversely curved in the form of a spiral with the calf shank extending upward anteriorly from the spiral to an upstanding upper end thereof. This creates a calf shank with an integrated ankle at the lower end thereof, when the calf shank is secured to the foot keel, with a variable radii response outcome similar to a parabola-shaped calf shank of the invention. The calf shank with spiral lower end is secured to the foot keel by way of a coupling element. The coupling element can include a stop to limit dorsiflexion of the calf shank in gait. In several embodiments the coupling element is monolithically formed with the forefoot portion of the foot keel. According to another feature of the invention the coupling element extends posteriorly as a cantilever over the midfoot portion and part of the hindfoot portion of the foot keel. The coupling element can be reversely curved upwardly to form an anterior facing concavity in which the lower end of the calf shank is housed, the reversely curved lower end of the calf shank being supported at its end from the coupling element. The resulting prosthesis has improved efficiency.

These and other features and advantages of the present invention become more apparent from a consideration of the following detailed description of disclosed example embodiments of the invention and the accompanying drawings.

BRIEF DESCRIPTION OF THE DRAWINGS

FIG. 1 is a schematic illustration representing the two adjacent radii of curvatures $R_1$ and $R_2$, one against the other, of a foot keel and calf shank of a prosthetic foot of the invention which creates a dynamic response capability and motion outcome of the foot in gait in the direction of arrow B which is perpendicular to the tangential line A connecting the two radii.

FIG. 2 is a view similar to FIG. 1 but showing the alignment of the two radii having been changed in the prosthetic foot according to the invention to increase the horizontal component and decrease the vertical component of the dynamic response capability and motion outcome of the foot in gait so that arrow $B_1$, perpendicular to tangential line $A_1$, is more horizontally directed than is the case depicted in FIG. 1.

FIG. 3 is a side view of a prosthetic foot according to an example embodiment of the invention with pylon adapter and pylon connected thereto for securing the foot to the lower leg of an amputee.

FIG. 29 is a top view of the prosthetic foot in FIG. 28.

FIG. 30 is a cross-sectional view of the prosthetic foot of FIGS. 28 and 29 taken along the line 30-30 in FIG. 29.

FIGS. 31A and 31B are sectional views of wedges of different thicknesses which may be used in the dorsiflexion stop of the coupling element as shown in FIG. 30.

BEST MODE FOR CARRYING OUT THE INVENTION

Figure 4:
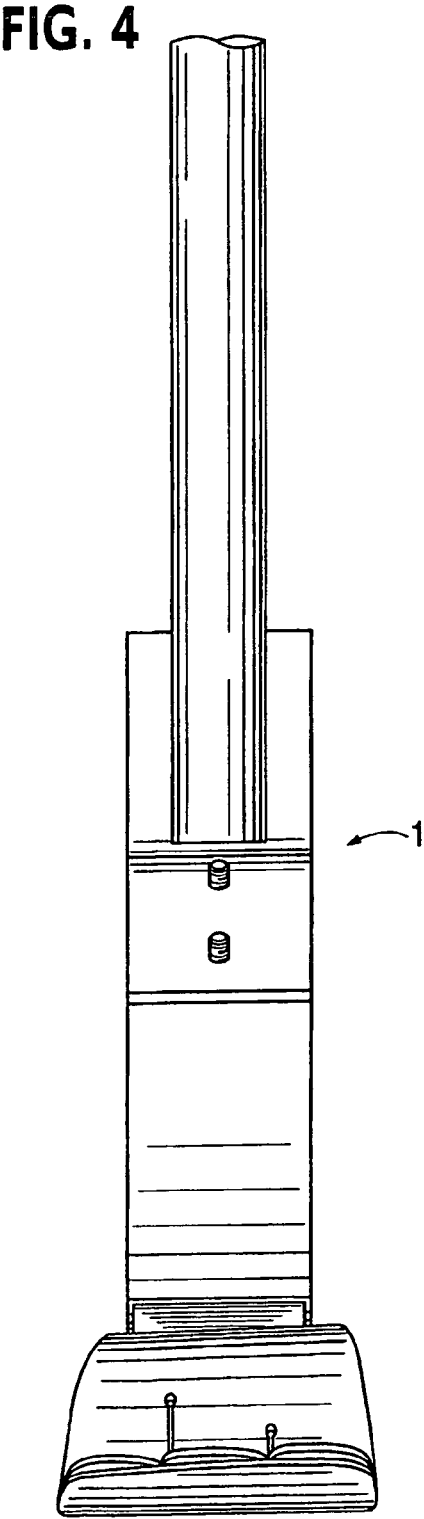
FIG. 4 is a front view of the prosthetic foot with pylon adapter and pylon of FIG. 3.
Figure 5:
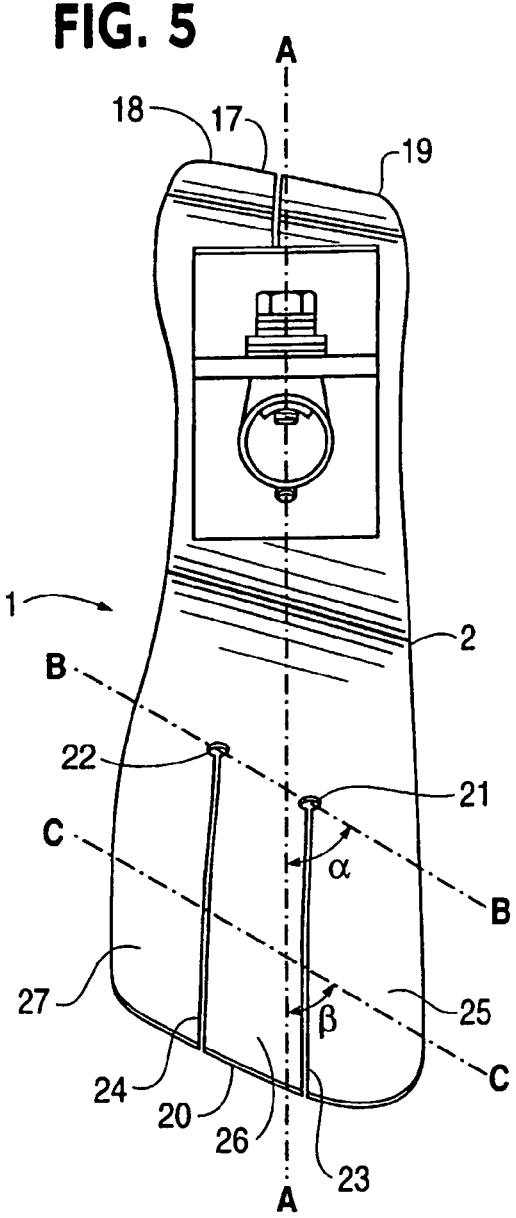
FIG. 5 is a top view of the embodiment of FIGS. 3 and 4.

Referring now to the drawings, a prosthetic foot 1 in the example embodiment of FIGS. 3-5 is seen to comprise a longitudinally extending foot keel 2 having a forefoot portion 3 at one end, a hindfoot portion 4 at an opposite end and an upwardly arched midfoot portion 5 extending between the forefoot and hindfoot portions. The midfoot portion 5 is upward convexly curved over its entire longitudinal extent between the forefoot and hindfoot portions in the example embodiment.

An upstanding calf shank 6 of the foot 1 is attached at a portion of a downward convexly curved lower end 7 thereof to a proximate, posterior surface of the keel midfoot portion 5 by way of a releasable fastener 8 and coupling element 11. The fastener 8 is a single bolt with nut and washers in the example embodiment, but could be a releasable clamp or other fastener for securely positioning and retaining the calf shank on the foot keel when the fastener is tightened.

Figure 8:
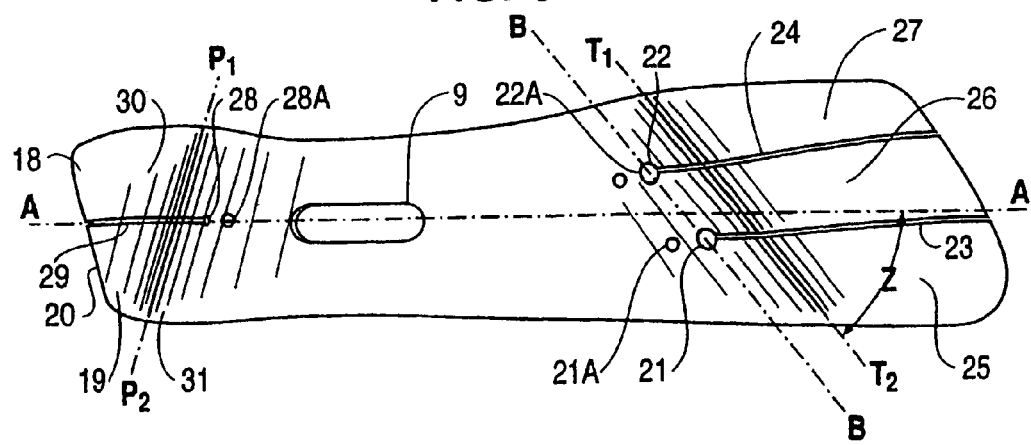
FIG. 8 is a bottom view of the foot keel in the prosthetic foot in FIG. 3 which. provides high low dynamic response characteristics as well as biplanar motion capabilities.
Figure 15:
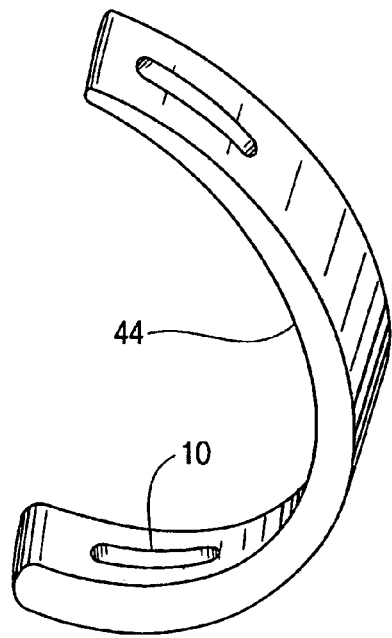
FIG. 15 is a side view from slightly above and to the front of a parabola shaped calf shank of the prosthetic foot of the invention, the thickness of the calf shank tapering toward its upper end.

A longitudinally extending opening 9 is formed in a proximate, posterior surface of the keel midfoot portion 5, see FIG. 8. A longitudinally extending opening 10 is also formed in the curved lower end 7 of the calf shank 6 like that shown in FIG. 15, for example. The releasable fastener 8 extends through the openings 9 and 10 which permit adjusting the alignment of the calf shank and the foot keel with respect to one another in the longitudinal direction, A-A in FIG. 5, when the fastener 8 is loosened or released for tuning the performance of the prosthetic foot to be task specific. Thus, the fastener 8, coupling element 11 and longitudinally extending openings 9 and 10 constitute an adjustable fastening arrangement for attaching the calf shank to the foot keel to form an ankle joint area of the prosthetic foot.

The effects of adjusting the alignment of the calf shank 6 and foot keel 2 are seen from a consideration of FIGS. 1 and 2, wherein the two radii $R_1$ and $R_2$, one next to another, represent the adjacent, facing, domed or convexly curved surfaces of the foot keel midportion 5 and the calf shank 6. When two such radii are considered one next to another, motion capability exists perpendicular to a tangential line, A in FIG. 1, $A_1$ in FIG. 2, drawn between the two radii. The interrelationship between these two radii determines a direction of motion outcomes. As a consequence, dynamic response force application of the foot 1 is dependent on this relationship. The larger the radius of a concavity, the more dynamic response capability. However, the tighter a radius, the quicker it responds.

The alignment capability of the calf shank and foot keel in the prosthetic foot of the invention allows the radii to be shifted so that horizontal or vertical linear velocities with the foot in athletic activities are affected. For example, to improve the horizontal linear velocity capability of the prosthetic foot 1, an alignment change can be made to affect the relationship of the calf shank's radius and the foot keel radius. That is, to improve the horizontal linear velocity characteristic, the bottom radius $R_2$, of the foot keel, is made more distal than its start position, FIG. 2 as compared with FIG. 1. This changes the dynamic response characteristics and motion outcomes of the foot 1 to be more horizontally directed and as a result greater horizontal linear velocity can be achieved with the same applied forces.

Figure 23:
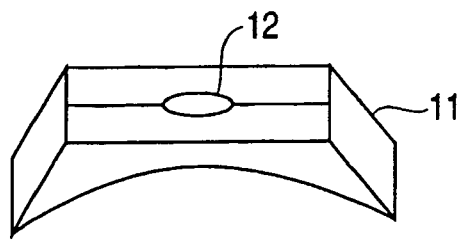
FIG. 23 is a side view, from slightly above, of a metal alloy or plastic coupling element used in the adjustable fastening arrangement of the invention for attaching the calf shank to the foot keel as shown in FIG. 3.
Figure 24:
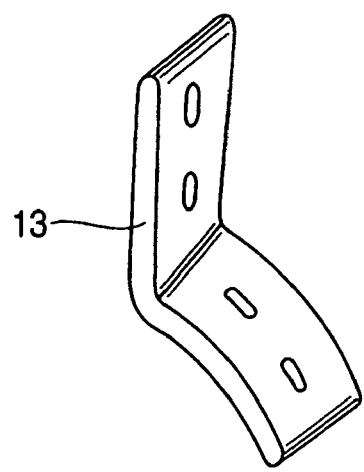
FIG. 24 is a view from the side and slightly to the front of a pylon adapter used on the prosthetic foot of FIGS. 3-5, and also useful with the foot of FIGS. 28 and 29, for connecting the foot to a pylon to be attached to an amputee's leg.

The amputee can, through practice, find a setting for each activity that meets his/her needs as these needs relate to horizontal and vertical linear velocities. A jumper and a basketball player, for example, need more vertical lift than a sprint runner. The coupling element 11 is a plastic or metal alloy alignment coupling (see FIGS. 3, 4 and 23) sandwiched between the attached foot keel 2 and calf shank 6. The releasable fastener 8 extends through a hole 12 in the coupling element. The coupling element extends along the attached portion of the calf shank and the proximate, posterior surface of the keel midfoot portion 5.

The curved lower end 7 of the calf shank 6 is in the shape of a parabola with the smallest radius of curvature of the parabola located at the lower end and extending upwardly, and initially anteriorly in the parabola shape. A posteriorly facing concavity is formed by the curvature of the calf shank as depicted in FIG. 3. The parabola shape is advantageous in that it has increased dynamic response characteristics in creating both improved horizontal linear velocity associated with the relatively larger radii proximal terminal end thereof, while having a smaller radius of curvature at its lower end for quicker response characteristics. The larger radii of curvature at the upper end of the parabola shape enable the tangential line A, explained with reference to FIGS. 1 and 2, to remain more horizontally oriented with changes in alignment, which creates improved horizontal linear velocity.

The parabolic shaped calf shank responds to initial contact ground forces in human gait by compressing or coiling in on itself. This makes the radii of the parabola curve smaller, and as a consequence, the resistance to compression is decreased. In contrast, as the parabolic shaped calf shank responds to heel off ground reaction forces (GRFs) in human gait by expanding, this makes the radii of the parabola curve larger and as a consequence resistance is much greater than the aforementioned compressive resistance. These resistances are associated with the human's anterior and posterior calf muscle function in human gait. At initial contact to foot flat of human gait, the smaller anterior calf muscle group responds to GRFs by eccentrically contracting to lower the foot to the ground and a dorsiflexion moment is created. From foot flat to toe off the larger posterior calf muscle group responds to GRFs also by eccentrically contracting and a greater plantar flexion moment is created. This moment size relates to the calf anterior and posterior muscle group difference in size. As a consequence, the prosthetic calf shank's resistance to the dorsiflexion and plantar flexion moments in human gait are mimicked and normal gait is achieved. The parabolic curves variable resistance capability mimics the human calf musculature function in human gait and running and jumping activities, and as a consequence prosthetic efficiency is achieved. Tests have shown that a prosthetic foot according to the invention produced 86% of non-pathological human ankle joint kinetic power generation, more than twice that obtained in tests of a conventional prosthetic foot of the aforementioned type having a posterior facing, convexly-curved ankle and shank. It is believed that at least one factor in this dramatic improvement in sagittal plane kinetic power generated by the prosthesis of the invention is that with the invention's anterior convexly curved resilient ankle and integral resilient shank, angular velocity is increased in response to compressing force in late mid-stance loading whereas in the prior art prosthesis angular velocity decrease in response to such loading. This improvement with the present invention lowers the energy expenditure by a user for walking, increases walking speed and allows a more normal gait.

A human being walks at approximately three miles per hour. A 4:00 minute miler runs at 12 miles per hour and a 10 second, 100 meter sprinter sprints at 21 miles per hour. This is a 1 to 4 to 7 ratio. The horizontal component of each task is greater as the velocity of the activity increases. As a consequence, the size of the prosthetic calf shank radii can be predetermined. A walker needs a smaller radii parabolic curved calf shank than a miler and a sprinter. A sprint runner needs a parabolic curved calf shank that is seven times as large. This relationship shows how to determine the parabolic radii for walkers, runners and sprinters. It is of significance because sprint runners have increased range of motion requirements and their calf shanks must be stronger to accept the increased loads associated with this activity. A wider or larger parabolic calf shank will be a relatively flatter curve, which equates to greater structural strength with increased range of motion.

A pylon adapter 13 is connected to the upper end of the calf shank 6 by fasteners 14. The adapter 13 in turn is secured to the lower end of pylon 15 by fasteners 16. Pylon 15 is secured to the lower limb of the amputee by a supporting structure (not shown) attached to the leg stump.

The forefoot, midfoot and hindfoot portions of the foot keel 2 are formed of a single piece of resilient material in the example embodiment. For example, a solid piece of material, plastic in nature, having shape-retaining characteristics when deflected by the ground reaction forces can be employed. More particularly, the foot keel and also the calf shank can be formed of laminated composite material having reinforcing fiber laminated with polymer matrix material. In particular, a high strength graphite, laminated with epoxy thermosetting resins, or extruded plastic utilized under the tradename of Delran, or degassed polyurethane copolymers, may be used to form the foot keel and also the calf shank. The functional qualities associated with these materials afford high strength with low weight and minimal creep. The thermosetting epoxy resins are laminated under vacuum utilizing prosthetic industry standards. The polyurethane copolymers can be poured into negative molds and the extruded plastic can be machined. Each material of use has its advantages and disadvantages. It has been found that the laminated composite material for the foot keel and the calf shank can also advantageously be a thermo-formed (prepreg) laminated composite material manufactured per industry standards, with reinforcing fiber and a thermoplastic polymer matrix material for superior mechanical expansion qualities. A suitable commercially available composite material of this kind is CYLON® made by Cytec Fiberite Inc. of Havre de Grace, Md. Alternatively, the foot keel and calf shank in this and the other embodiments disclosed herein can be made of resilient metal alloy, for example, of grade 5 titanium alloy which has been solution heat treated and over aged (STOA) and shot peened with specifications that increase the fatigue life through the addition of compressive stresses on the surface.

The resilient material's physical properties as they relate to stiffness, flexibility and strength are all determined by the thickness of the material. A thinner material will deflect easier than a thicker material of the same density. The material utilized, as well as the physical properties, are associated with the stiffness to flexibility characteristics in the prosthetic foot keel and calf shank. The thickness of the foot keel and calf shank are uniform or symmetrical in the example embodiment of FIGS. 3-5, but the thickness along the length of these components can be varied as discussed below, such as by making the hindfoot and forefoot areas thinner and more responsive to deflection in the midfoot region.

To aid in providing the prosthetic foot 1 with a high low dynamic response capability, the midfoot portion 5 is formed by a longitudinal arch such that the medial aspect of the longitudinal arch has a relatively higher dynamic response capability than the lateral aspect of the longitudinal arch. For this purpose, in the example embodiment, the medial aspect of the longitudinal arch concavity is larger in radius than the lateral aspect thereof.

The interrelationship between the medial to lateral radii size of the longitudinal arch concavity of the midfoot portion 5 is further defined as the anterior posterior plantar surface weight bearing surface areas of the foot keel 2. The line $T_1$-$T_2$ on the anterior section of 5 in FIG. 8 represents the anterior plantar surface weight bearing area. Line $P_1$-$P_2$ represents the posterior plantar weight-bearing surface of 5. The plantar weight bearing surfaces on the lateral side of the foot would be represented by the distance between $T_1$-$P_1$. The plantar weight bearing surfaces on the medial side of the foot 2 are represented by the distance between $P_2$-$T_2$. The distances represented by $T_1$-$P_1$ and $P_2$-$T_2$ determine the radii size, and as a result the high low dynamic response interrelationship is determined and can be influenced by converging or diverging these two lines $T_1$-$T_2$ to $P_1$-$P_2$. As a result, high low dynamic response can be determined in structural design.

The posterior end 17 of the hindfoot portion 4 is shaped in an upwardly curved arch that reacts to ground reaction forces during heel strike by compressing for shock absorption. The heel formed by the hindfoot portion 4 is formed with a posterior lateral corner 18 which is more posterior and lateral than the medial corner 19 to encourage hindfoot eversion during initial contact phase of gait. The anterior end 20 of the forefoot portion 3 is shaped in an upwardly curved arch to simulate the human toes being dorsiflexed in the heel rise toe off position of the late stance phase of gait. Rubber or foam pads 53 and 54 are provided on the lower forefoot and hindfoot as cushions.

Improved biplanar motion capability of the prosthetic foot is created by medial and lateral expansion joint holes 21 and 22 extending through the forefoot portion 3 between dorsal and plantar surfaces thereof. Expansion joints 23 and 24 extend forward from respect ones of the holes to the anterior edge of the forefoot portion to form medial, middle and lateral expansion struts 25-27 which create improved biplanar motion capability of the forefoot portion of the foot keel. The expansion joint holes 21 and 22 are located along a line, B-B in FIG. 5, in the transverse plane which extends at an angle $\alpha$ of 35° to the longitudinal axis A-A of the foot keel with the medial expansion joint hole 21 more anterior than the lateral expansion joint hole 22.

The angle $\alpha$ of line B-B to longitudinal axis A-A in FIG. 5 can be as small as 15° and still derive a high low dynamic response. As this angle $\alpha$ changes, so should the angle Z of the line $T_1$-$T_2$ in FIG. 8. The expansion joint holes 21 and 22 as projected on a sagittal plane are inclined at an angle of 45° to the transverse plane with the dorsal aspect of the holes being more anterior than the plantar aspect. With this arrangement, the distance from the releasable fastener 8 to the lateral expansion joint hole 22 is shorter than the distance from the releasable fastener to the medial expansion joint hole 21 such that the lateral portion of the prosthetic foot 1 has a shorter toe lever than the medial for enabling midfoot high and low dynamic response. In addition, the distance from the releasable fastener 8 to the lateral plantar weight bearing surface as represented by $T_1$, line is shorter than the distance from the releasable fastener to the medial plantar surface weight bearing surface as represented by the line $T_2$—such that the lateral portion of the prosthetic foot 1 has a shorter toe lever than the medial for enabling midfoot high low dynamic response.

The anterior of the hindfoot portion 4 of the foot keel 2 further includes an expansion joint hole 28 extending through the hindfoot portion 4 between dorsal and plantar surfaces thereof. An expansion joint 29 extends posteriorly from the hole 28 to the posterior edge of the hindfoot portion to form expansion struts 30 and 31. These create improved biplanar motion capability of the hindfoot portion of the foot.

A dorsal aspect of the midfoot portion 5 and the forefoot portion 3 of the foot keel 2 form the upwardly facing concavity, 32 in FIG. 3, so that it mimics in function the fifth ray axis of motion of a human foot. That is, the concavity 32 has a longitudinal axis C-C which is oriented at an angle β of 15° to 35° to the longitudinal axis A-A of the foot keel with the medial being more anterior than the lateral to encourage fifth ray motion in gait as in the oblique low gear axis of rotation of the second to fifth metatarsals in the human foot.

The importance of biplanar motion capability can be appreciated when an amputee walks on uneven terrain or when the athlete cuts medially or laterally on the foot. The direction of the ground force vector changes from being sagittally oriented to having a frontal plane component. The ground will push medially in opposite direction to the foot pushing laterally. As a consequence to this, the calf shank leans medially and weight is applied to the medial structure of the foot keel. In response to these pressures, the medial expansion joint struts 25 and 31 of the foot keel 2 dorsiflex (deflect upward) and invert, and the lateral expansion joint struts 27 and 30 plantar flex (deflect downwards) and evert. This motion tries to put the plantar surface of the foot flat on the ground (plantar grade).

Figure 6:
FIG. 6 is a side view of another foot keel of the invention, especially for sprinting, which may be used in the prosthetic foot of the invention.
Figure 7:
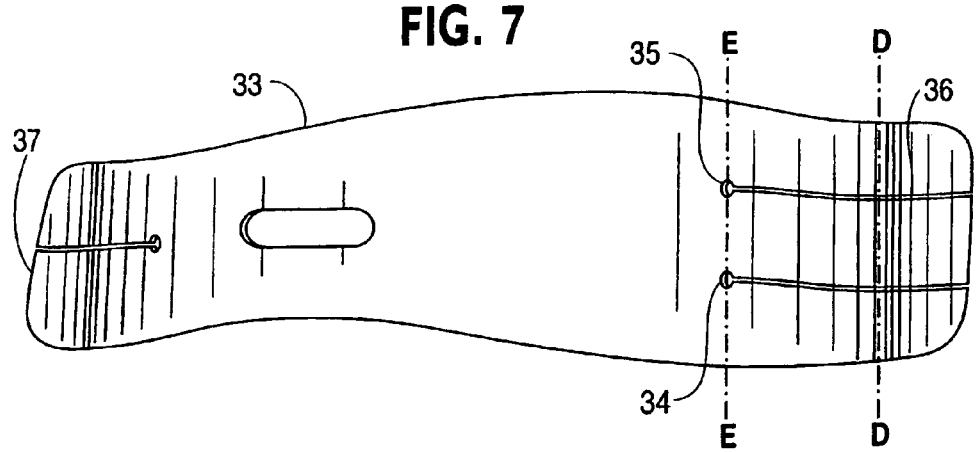
FIG. 7 is a top view of the foot keel of FIG. 6.

Another foot keel 33 of the invention, especially for sprinting, may be used in the prosthetic foot of the invention, see FIGS. 6 and 7. The body's center of gravity in a sprint becomes almost exclusively sagittal plane oriented. The prosthetic foot does not need to have a low dynamic response characteristic. As a consequence, the 15° to 35° external rotation orientation of the longitudinal axis of the forefoot, midfoot concavity as in foot keel 2 is not needed. Rather, the concavity's longitudinal axis D-D orientation should become parallel to the frontal plane as depicted in FIGS. 6 and 7. This makes the sprint foot respond in a sagittal direction only. Further, the orientation of the expansion joint holes 34 and 35 in the forefoot and midfoot portions, along line E-E, is parallel to the frontal plane, i.e., the lateral hole 35 is moved anteriorly and in line with the medial hole 34 and parallel to the frontal plane. The anterior terminal end 36 of the foot keel 33 is also made parallel to the frontal plane. The posterior terminal heel area 37 of the foot keel is also parallel to the frontal plane. These modifications effect in a negative way the multi-use capabilities of the prosthetic foot. However, its performance characteristics become task specific. Another variation in the sprint foot keel 33 is in the toe, ray region of the forefoot portion of the foot where 15° of dorsiflexion in the foot keel 2 are increased to 25-40° of dorsiflexion in foot keel 33.

Figure 9:
FIG. 9 is a side view of an additional foot keel of the invention for the prosthetic foot particularly useful for sprinting by an amputee that has had a Symes amputation of the foot.
Figure 10:
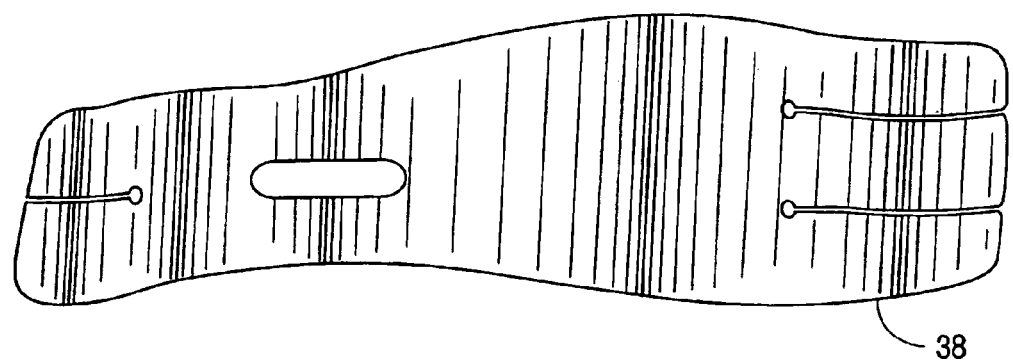
FIG. 10 is a top view of the foot keel of FIG. 9.
Figure 11:
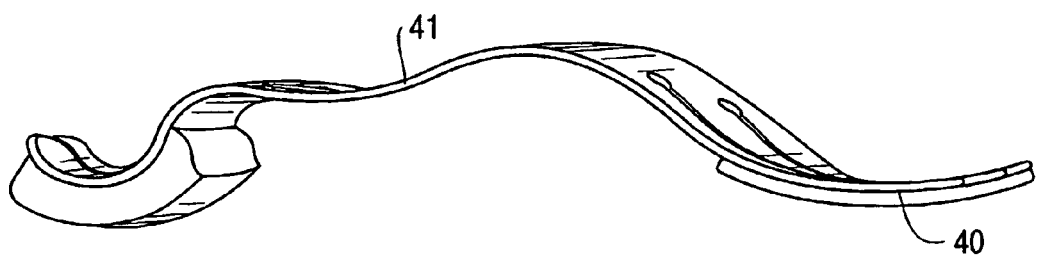
FIG. 11 is a further variation of foot keel for the prosthetic foot of the invention for a Symes amputee, the foot keel providing the prosthetic foot with high low dynamic response characteristics as well as biplanar motion capabilities.
Figure 12:
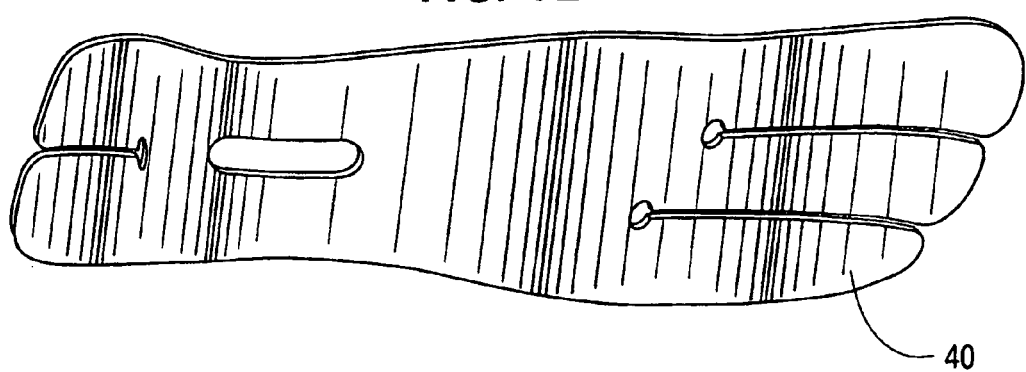
FIG. 12 is a top view of the foot keel of FIG. 11.

FIGS. 9 and 10 show an additional foot keel 38 of the invention for the prosthetic foot particularly useful for sprinting by an amputee that has had a Symes amputation of the foot. For this purpose, the midfoot portion of the foot keel 38 includes a posterior, upwardly facing concavity 39 in which the curved lower end of the calf shank is attached to the foot keel by way of the releasable fastener. This foot keel can be utilized by all lower extremity amputees. The foot keel 38 accommodates the longer residual limb associated with the Symes level amputee. Its performance characteristics are distinctively quicker in dynamic response capabilities. Its use is not specific to this level of amputation. It can be utilized on all transtibial and transfemoral amputations. The foot keel 40 in the example embodiment of FIGS. 11 and 12 also has a concavity 41 for a Symes amputee, the foot keel providing the prosthetic foot with high low dynamic response characteristic as well as biplanar motion capabilities like those of the example embodiment in FIGS. 3-5 and 8.

The functional characteristics of the several foot keels for the prosthetic foot 1 are associated with the shape and design features as they relate to concavities, convexities, radii size, expansion, compression, and material physical properties—all of these properties relating, to reacting to, ground forces in walking, running and jumping activities.

Figure 13:
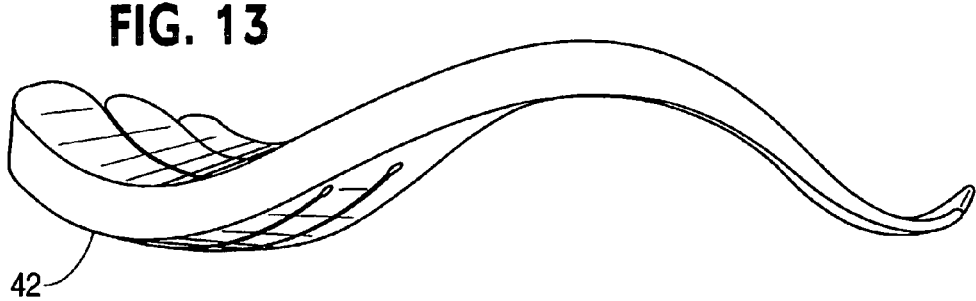
FIG. 13 is a side view of a foot keel of the invention wherein the thickness of the keel tapers, e.g., is progressively reduced, from the midfoot portion to the hindfoot portion of the keel.
Figure 14:
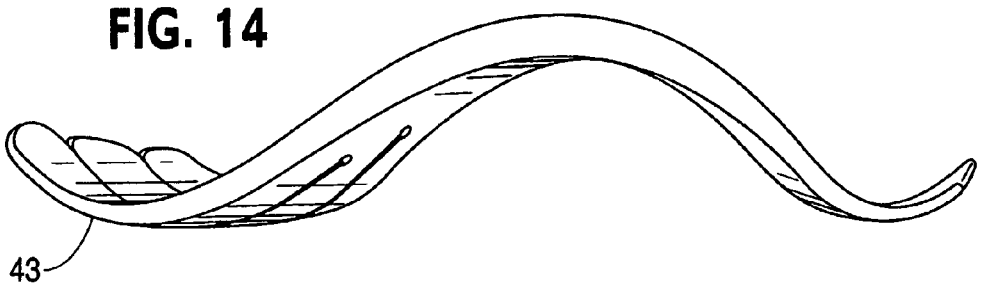
FIG. 14 is a side view of another form of the foot keel wherein the thickness tapers from the midfoot toward both the forefoot and hindfoot of the keel.
Figure 16:
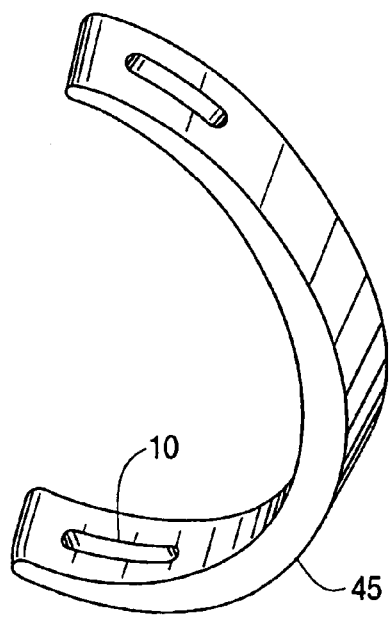
FIG. 16 is a side view like FIG. 15 but showing another calf shank tapered from the middle towards both its upper and lower ends.
Figure 17:
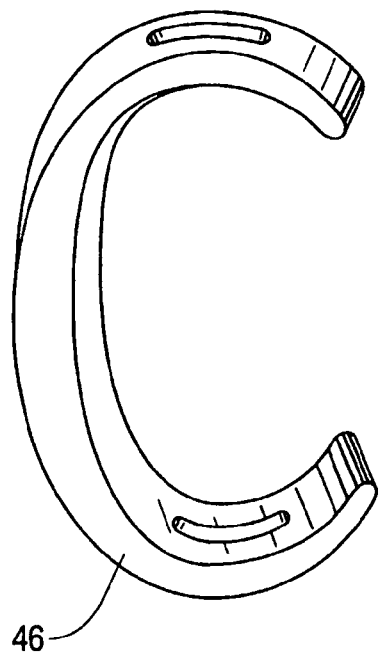
FIG. 17 is a side view of a C-shaped calf shank for the prosthetic foot, the calf shank thickness tapering from the middle towards both its upper and lower ends.
Figure 18:
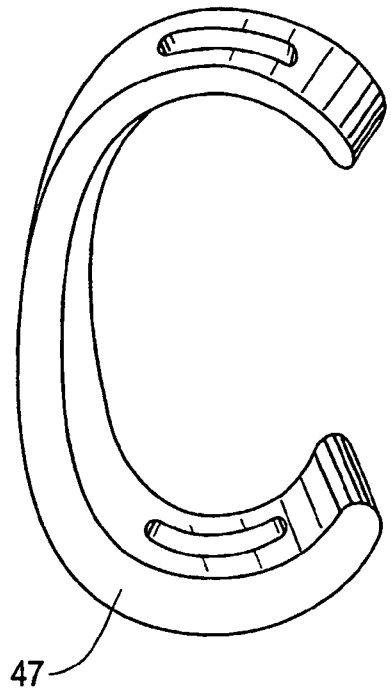
FIG. 18, is a side view of another example of a C-shaped calf shank for the prosthetic foot, the thickness of the calf shank being progressively reduced from its midportion to its upper end.
Figure 19:
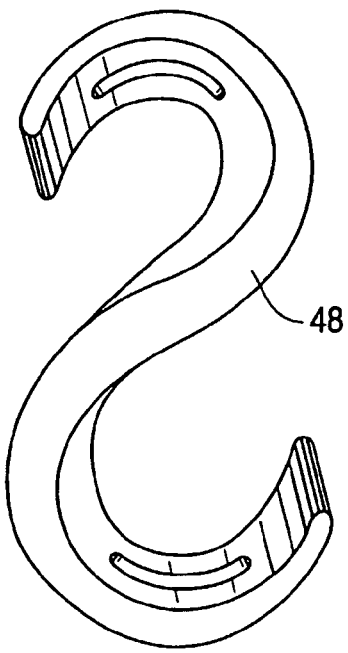
FIG. 19 is a side view of an S-shaped calf shank for the prosthetic foot, both ends being progressively reduced in thickness from the middle thereof.
Figure 20:
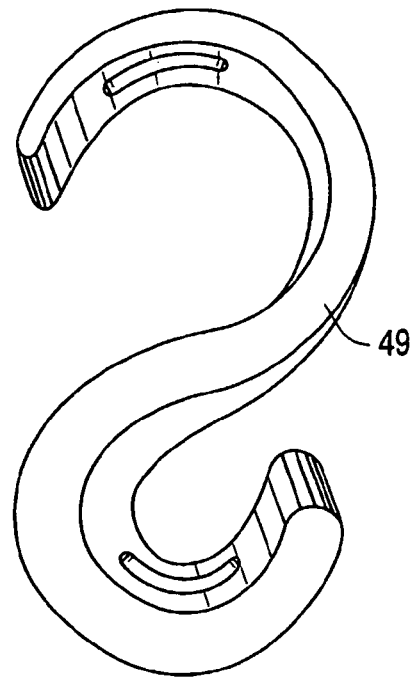
FIG. 20 is a further example of an S-shaped calf shank which is tapered in thickness only at its upper end.
Figure 21:
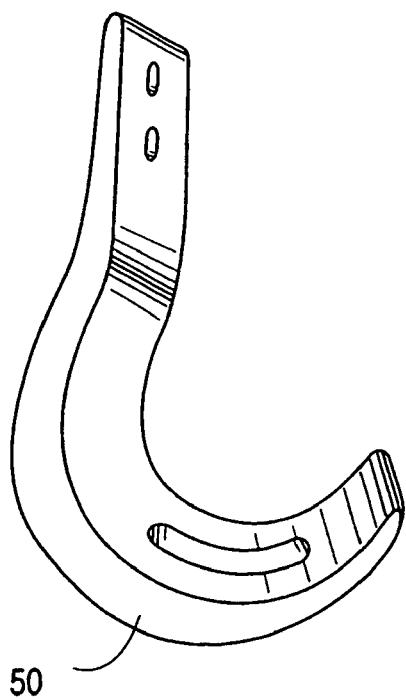
FIG. 21 is a side view of a J-shaped calf shank, tapered at each end, for the prosthetic foot of the invention.
Figure 22:
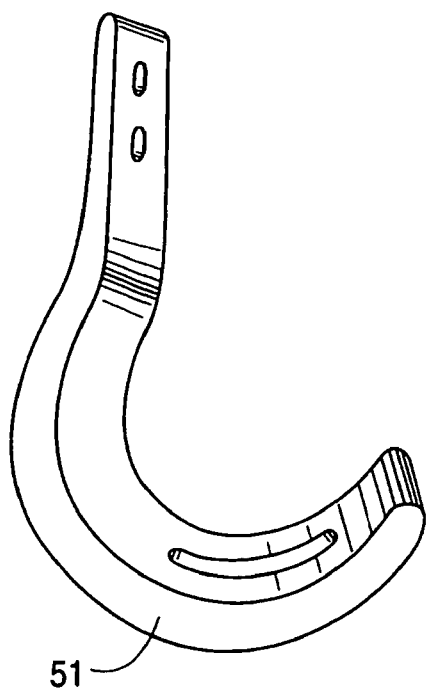
FIG. 22 is a view like FIG. 21 but showing a J-shaped calf shank which is progressively reduced in thickness towards only its upper end.

The foot keel 42 in FIG. 13 is like that in the example embodiment of FIGS. 3-5 and 8, except that the thickness of the foot keel is tapered from the midfoot portion to the posterior of the hindfoot. The foot keel 43 in FIG. 14 has its thickness progressively reduced or tapered at both its anterior and posterior ends. Similar variations in thickness are shown in the calf shank 44 of FIG. 15 and the calf shank 45 of FIG. 16 which may be used in the prosthetic foot 1. Each design of the foot keel and calf shank create different functional outcomes, as these function outcomes relate to the horizontal and vertical linear velocities which are specific to improving performance in varied athletic related tasks. The capability of multiple calf shank configurations and adjustments in settings between the foot keel and the calf shank create a prosthetic foot calf shank relationship that allows the amputee and/or the prosthetist the ability to tune the prosthetic foot for maximum performance in a selected one of a wide variety of walking and recreational activities.

Other calf shanks for the prosthetic foot 1 are illustrated in FIGS. 17-22 and include C-shaped calf shanks 46 and 47, S-shaped calf shanks 48 and 49 and modified J-shaped calf shanks 50 and 51. The upper end of the calf shank could also have a straight vertical end with a pyramid attachment plate attached to this proximal terminal end. A male pyramid could be bolted to and through this vertical end of the calf shank. Plastic or aluminum fillers to accept the proximal male pyramid and the distal foot keel could also be provided in the elongated openings at the proximal and distal ends of the calf shank. The prosthetic foot of the invention is a modular system preferably constructed with standardized units or dimensions for flexibility and variety in use.

All track related running activities take place in a counterclockwise direction. Another, optional feature of the invention takes into account the forces acting on the foot advanced along such a curved path. Centripetal acceleration acts toward the center of rotation where an object moves along a curved path. Newton's third law is applied for energy action. There is an equal and opposite reaction. Thus, for every "center seeking" force, there is a "center fleeing" force. The centripetal force acts toward the center of rotation and the centrifugal force, the reaction force, acts away from the center of rotation. If an athlete is running around the curve on the track, the centripetal force pulls the runner toward the center of the curve while the centrifugal force pulls away from the center of the curve. To counteract the centrifugal force which tries to lean the runner outward, the runner leans inward. If the direction of rotation of the runner on the track is always counter-clockwise, then the left side is the inside of the track. As a consequence, according to a feature of the present invention, the left side of the right and left prosthetic foot calf shanks can be made thinner than the right side and the amputee runner's curve performance could be improved.

The foot keels 2, 33, 38, 42 and 43 in the several embodiments, are each 29 cm long with the proportions of the shoe 1 shown to scale in FIGS. 3, 4 and 5, and in the several views of the different calf shanks and foot keels. However, as will be readily understood by the skilled artisan, the specific dimensions of the prosthetic foot can be varied depending on the size, weight and other characteristics of the amputee being fitted with the foot. The human foot, ankle, shank and soft supporting tissues are loaded with kinetic energy during the stance phase of the gait and running cycle. A prosthetic calf shank that is longer in length has more elastic energy storage capacity. As a consequence, more ankle joint kinetic power is utilized to do the work of walking, running and jumping. Therefore, the prosthetic calf shank can be attached to the most proximal regions of the amputee's residual limb socket; for example, to the tibia tubercle height.

The operation of the prosthetic foot 1 in walking and running stance phase gait cycles will now be considered. Newton's three laws of motion, that relate to law of inertia, acceleration and action-reaction, are the basis for movement kinematics in the foot 2. From Newton's third law, the law of action-reaction, it is known that the ground pushes on the foot in a direction equal and opposite to the direction the foot pushes on the ground. These are known as ground reaction forces. Many scientific studies have been done on human gait, running and jumping activities. Force plate studies show us that Newton's third law occurs in gait. From these studies, we know the direction the ground pushes on the foot.

The stance phase of walking/running activities can be further broken down into deceleration and acceleration phases. When the prosthetic foot touches the ground, the foot pushes anteriorly on the ground and the ground pushes back in an equal and opposite direction—that is to say the ground pushes posteriorly on the prosthetic foot. This force makes the prosthetic foot move. The stance phase analysis of walking and running activities begins with the contact point being the posterior lateral corner 18, FIGS. 5 and 8, which is offset more posteriorly and laterally than the medial side of the foot. This offset at initial contact causes the foot to evert and the calf shank to plantar flex. The calf shank always seeks a position that transfers the body weight through its shank, e.g., it tends to have its long vertical member in a position to oppose the ground forces. This is why it moves posteriorly-plantar flexes to oppose the ground reaction force which is pushing posteriorly on the foot.

The ground forces cause calf shanks 6, 44, 45, 46, 47, 50 and 51 and those in the other embodiments to compress with the proximal end moving posterior. In calf shanks 48 and 49, if the distal concavity is compressed in response to the ground reaction forces the proximal concavity would expand and the entire calf shank unit would move posteriorly. The initial loading ground forces cause the lower end of the calf shank to compress with the proximal end moving posteriorly. The calf shank lower tight radius compresses simulating human ankle joint plantar flexion and the forefoot is lowered by compression to the ground. At the same time to the posterior aspect of keel, as represented by hindfoot 4, depicted by 17 compresses upward through compression. Both of these compressive forces act as shock absorbers. This shock absorption is further enhanced by the offset posterior lateral heel 18 which causes the foot to evert, which also acts as a shock absorber, once the calf shank has stopped moving into plantar flexion and with the ground pushing posteriorly on the foot.

The compressed members of the foot keel and calf shank then start to unload—that is they seek their original shape and the stored energy is released—which causes the calf shank proximal end to move anteriorly in an accelerated manner. As the calf shank approaches its vertical starting position, the ground forces change from pushing posteriorly to pushing vertically upward against the foot. Since the prosthetic foot has posterior and anterior plantar surface weight bearing areas and these areas are connected by a non-weight bearing long arch shaped midportion, the vertically directed forces from the prosthesis cause the long arch shaped midportion to load by expansion. The posterior and anterior weight-bearing surfaces diverge. These vertically directed forces are being stored in the long arch midportion of the foot—as the ground forces move from being vertical in nature to anteriorly directed. The lower end of the calf shank expands—simulating ankle dorsiflexion. This causes the prosthetic foot to pivot off of the anterior plantar weight-bearing surface. As weight unloading occurs, the long arch of the midfoot portion 5 changes from being expanded and it seeks its original shape which creates a simulated plantar flexor muscle group burst. This releases the stored vertical compressed force energy into improved expansion capabilities.

The long arch of the foot keel and the calf shank resist expansion of their respective structures. As a consequence, the calf shank anterior progression is arrested and the foot starts to pivot off the anterior plantar surface weight-bearing area. The expansion of the midfoot portion of the foot keel has as high and low response capability in the case of the foot keels in the example embodiments of FIGS. 3-5 and 8, FIGS. 11 and 12, FIG. 13 and FIG. 14. Since the midfoot forefoot transitional area of these foot keels is deviated 15° to 35° externally from the long axis of the foot, the medial long arch is longer than the lateral long arch. This is important because in the normal foot, during acceleration or deceleration, the medial aspect of the foot is used.

The prosthetic foot longer medial arch has greater dynamic response characteristic than the lateral. The lateral shorter toe lever is utilized when walking or running at slower speeds. The body's center of gravity moves through space in a sinusoidal curve. It moves medial, lateral, proximal and distal. When walking or running at slower speeds, the body's center of gravity moves more medial and lateral than when walking or running fast. In addition, momentum or inertia is less and the ability to overcome a higher dynamic response capability is less. The prosthetic foot of the invention is adapted to accommodate these principles in applied mechanics.

In addition, in the human gait cycle at midstance the body's center of gravity is as far lateral as it will go. From midstance through toe off the body's center of gravity (BCG) moves from lateral to medial. As a consequence, the body's center of gravity progresses over the lateral side of the foot keel 2. First (low gear) and as the BCG progresses forward, it moves medially on foot keel 2 (high gear). As a consequence, the prosthetic foot keel 2 has an automatic transmission effect. That is to say, it starts in low gear and moves into high gear every step the amputee takes.

As the ground forces push anteriorly on the prosthetic foot which is pushing posteriorly on the ground, as the heel begins to rise the anterior portion of the long arch of the midfoot portion is contoured to apply these posteriorly directed forces perpendicular to its plantar surface. This is the most effective and efficient way to apply these forces. The same can be said about the posterior hindfoot portion of the prosthetic foot. It is also shaped so that the posteriorly directed ground forces at initial contact are opposed with the foot keel's plantar surface being perpendicular to their applied force direction.

In the later stages of heel rise, toe off walking and running activities, the ray region of the forefoot portion is dorsiflexed 15°-35°. This upwardly extending arc allows the anteriorly directed ground forces to compress this region of the foot. This compression is less resisted than expansion and a smooth transition occurs to the swing phase of gait and running with the prosthetic foot. In later stages of stance phase of gait, the expanded calf shank and the expanded midfoot long arch release their stored energy adding to the propulsion of the amputee's soon to be swinging lower extremity.

One of the main propulsion mechanisms in human gait is called the active propulsion phase. As the heel lifts, the body weight is now forward of the support limb and the center of gravity is falling. As the body weight drops over the forefoot rocker FIG. 5, line C-C there is a downward acceleration, which results in the highest vertical force received by the body. Acceleration of the leg forward of the ankle, associated with lifting of the heel, results in a posterior shear against the ground. As the center of pressure moves anterior to the metatarsal heads axis of rotation the effect is an ever-increasing dorsiflexion torque. This creates a full forward fall situation that generates the major progression force used in walking. The signs of effective ankle function during the active propulsion are heel lift, minimal ankle joint motion, and a nearly neutral ankle position. A stable midfoot is essential for normal sequencing in heel lift.

The posterior aspect of the hindfoot and the forefoot region of the foot keel incorporate expansion joint holes and expansion joint struts in several of the embodiments as noted previously. The orientation of the expansion joint holes act as a mitered hinge and biplanar motion capabilities are improved for improving the total contact characteristics of the plantar surface of the foot when walking on uneven terrain.

The Symes foot keels in FIGS. 9-12 are distinctively different in dynamic response capabilities—as these capabilities are associated with walking, running and jumping activities. These foot keels differ in four distinct features. These include the presence of a concavity in the proximate, posterior of the midfoot portion for accommodating the Symes distal residual limb shape better than a flat surface. This concavity also lowers the height of the foot keel which accommodates the longer residual limb that is associated with the Symes level amputee. The alignment concavity requires that the corresponding anterior and posterior radii of the arched foot keel midportion be more aggressive and smaller in size. As a consequence, all of the midfoot long arch radii and the hindfoot radii are tighter and smaller. This significantly affects the dynamic response characteristics. The smaller radii create less potential for a dynamic response. However, the prosthetic foot responds quicker to all of the aforementioned walking, running and jumping ground forces. The result is a quicker foot with less dynamic response.

Improved task specific athletic performance can be achieved with alignment changes using the prosthetic foot of the invention, as these alignment changes affect the vertical and horizontal components of each task. The human foot is a multi-functional unit—it walks, runs and jumps. The human tibia fibula calf shank structure on the other hand is not a multi-functional unit. It is a simple lever which applies its forces in walking, running and jumping activities parallel to its long proximal-distal orientation. It is a non-compressible structure and it has no potential to store energy. On the other hand, the prosthetic foot of the invention has dynamic response capabilities, as these dynamic response capabilities are associated with the horizontal and vertical linear velocity components of athletic walking, running and jumping activities and out-performing the human tibia and fibula. As a consequence, the possibility exists to improve amputee athletic performance. For this purpose, according to the present invention, the fastener 8 is loosened and the alignment of the calf shank and the foot keel with respect to one another is adjusted in the longitudinal direction of the foot keel. Such a change is shown in connection with FIGS. 1 and 2. The calf shank is then secured to the foot keel in the adjusted position with the fastener 8. During this adjustment, the bolt of the fastener 8 slides relative to one or both of the opposed, relatively longer, longitudinally extending openings 9 and 10 in the foot keel and calf shank, respectively.

An alignment change that improves the performance characteristic of a runner who makes initial contact with the ground with the foot flat as in a midfoot strike runner, for example, is one wherein the foot keel is slid anterior relative to the calf shank and the foot plantar flexed on the calf shank. This new relationship improves the horizontal component of running. That is, with the calf shank plantar flexed to the foot, and the foot making contact with the ground in a foot flat position as opposed to initially heel contact, the ground immediately pushes posteriorly on the foot that is pushing anteriorly on the ground. This causes the calf shank to move rapidly forward (by expanding) and downwardly. Dynamic response forces are created by expansion which resists the calf shank's direction of initial movement. As a consequence, the foot pivots over the metatarsal plantar surface weight-bearing area. This causes the midfoot region of the keel to expand which is resisted more than compression. The net effect of the calf shank expansion and the midfoot expansion is that further anterior progression of the calf shank is resisted which allows the knee extenders and hip extenders in the user's body to move the body's center of gravity forward and proximal in a more efficient manner (i.e., improved horizontal velocity). In this case, more forward than up than in the case of a heel toe runner whose calf shank's forward progression is less resisted by the calf shank starting more dorsiflexed (vertical) than a foot flat runner.

To analyze the sprint foot in function, an alignment change of the calf shank and foot keel is made. Advantage is taken of the foot keel having all of its concavities with their longitudinal axis orientation parallel to the frontal plane. The calf shank is plantar flexed and slid posterior on the foot keel. This lowers the distal circles even further than on the flat foot runner with the multi-use foot keel like that in FIGS. 3-5 and 8, for example. As a consequence, there is even greater horizontal motion potential and the dynamic response is directed into this improved horizontal capability.

The sprinters have increased range of motion, forces and momentum (inertia)—momentum being a prime mover. Since their stance phase deceleration phase is shorter than their acceleration phase, increased horizontal linear velocities are achieved. This means that at initial contact, when the toe touches the ground, the ground pushes posteriorly on the foot and the foot pushes anteriorly on the ground. The calf shank which has increased forces and momentum is forced into even greater flexion and downward movement than the initial contact foot flat runner. As a consequence to these forces, the foot's long arch concavity is loaded by expansion and the calf shank is loaded by expansion. These expansion forces are resisted to a greater extent than all the other previously mentioned forces associated with running. As a consequence, the dynamic response capability of the foot is proportional to the force applied. The human tibia fibula calf shank response is only associated with the energy force potential—it is a straight structure and it cannot store energy. These expansion forces in the prosthetic foot of the invention in sprinting are greater in magnitude than all the other previously mentioned forces associated with walking and running. As a consequence, the dynamic response capability of the foot is proportional to the applied forces and increased amputee athletic performance, as compared with human body function, is possible.

Figure 25:
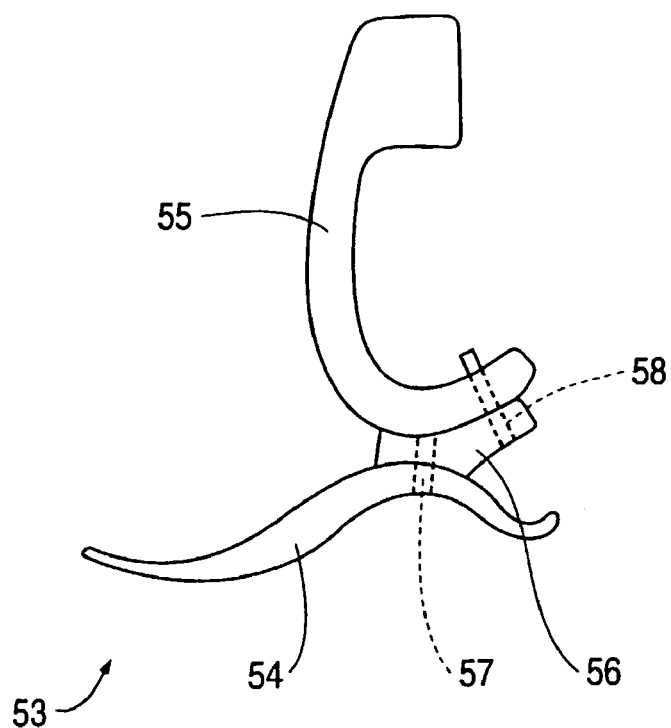
FIG. 25 is a side view of another prosthetic foot of the invention similar to that in FIG. 3, but showing use of a coupling element with two releasable fasteners spaced longitudinally connecting the element to the calf shank and foot keel, respectively.

The prosthetic foot 53 depicted in FIG. 25 is like that in FIG. 3 except for the adjustable fastening arrangement between the calf shank and the foot keel and the construction of the upper end of the calf shank for connection to the lower end of a pylon. In this example embodiment, the foot keel 54 is adjustably connected to the calf shank 55 by way of plastic or metal alloy coupling element 56. The coupling element is attached to the foot keel and calf shank by respective releasable fasteners 57 and 58 which are spaced from one another in the coupling element in a direction along the longitudinal direction of the foot keel. The fastener 58 joining the coupling element to the calf shank is more posterior than the fastener 57 joining the foot keel and the coupling element. By increasing the active length of the calf shank in this way, the dynamic response capabilities of the calf shank itself are increased. Changes in alignment are made in cooperation with longitudinally extending openings in the calf shank and foot keel as in other example embodiments.

The upper end of the calf shank 55 is formed with an elongated opening 59 for receiving a pylon 15. Once received in the opening, the pylon can be securely clamped to the calf shank by tightening bolts 60 and 61 to draw the free side edges 62 and 63 of the calf shank along the opening together. This pylon connection can be readily adjusted by loosening the bolts, telescoping the pylon relative to the calf shank to the desired position and reclamping the pylon in the adjusted position by tightening the bolts.

Figure 26:
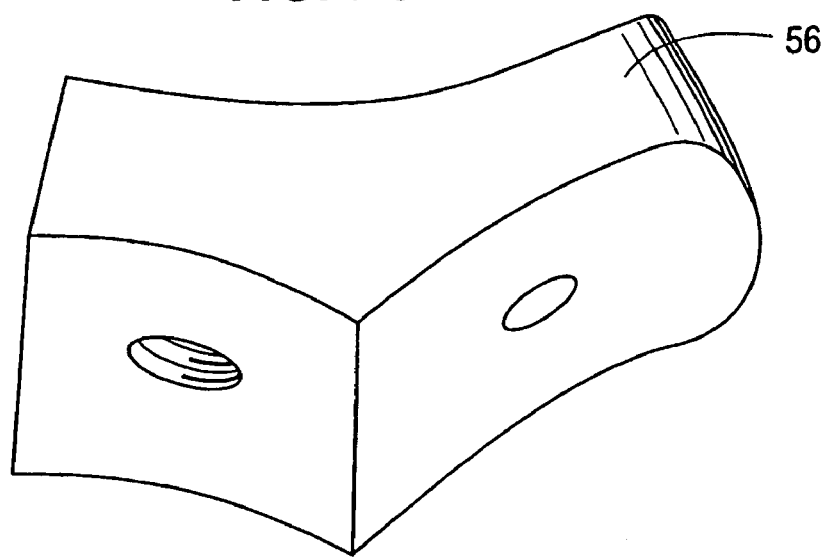
FIG. 26 is an enlarged side view of the coupling element in FIG. 25.
Figure 27:
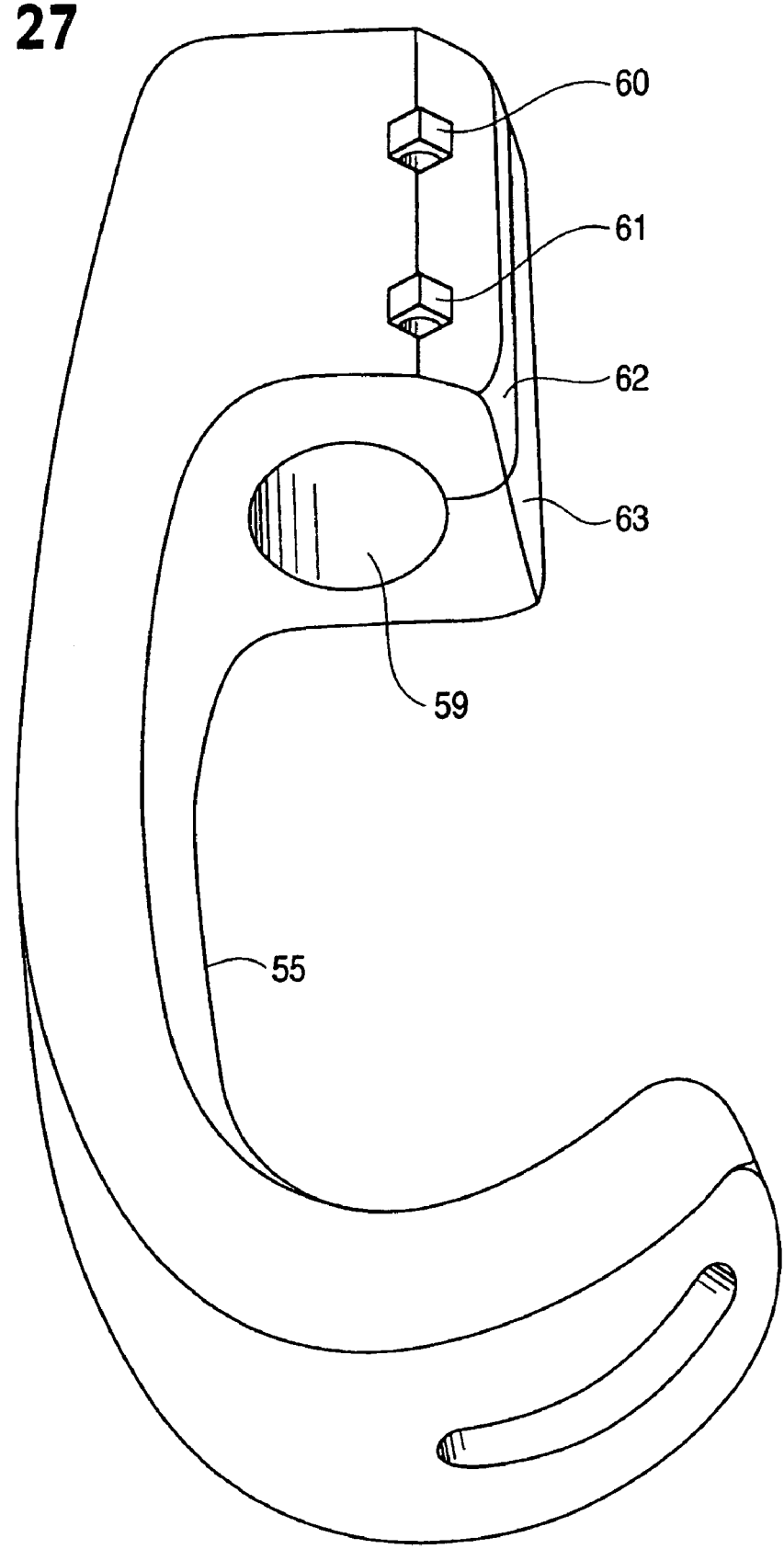
FIG. 27 is an enlarged side view of the calf shank of the prosthetic foot of FIG. 25.
Figure 28:
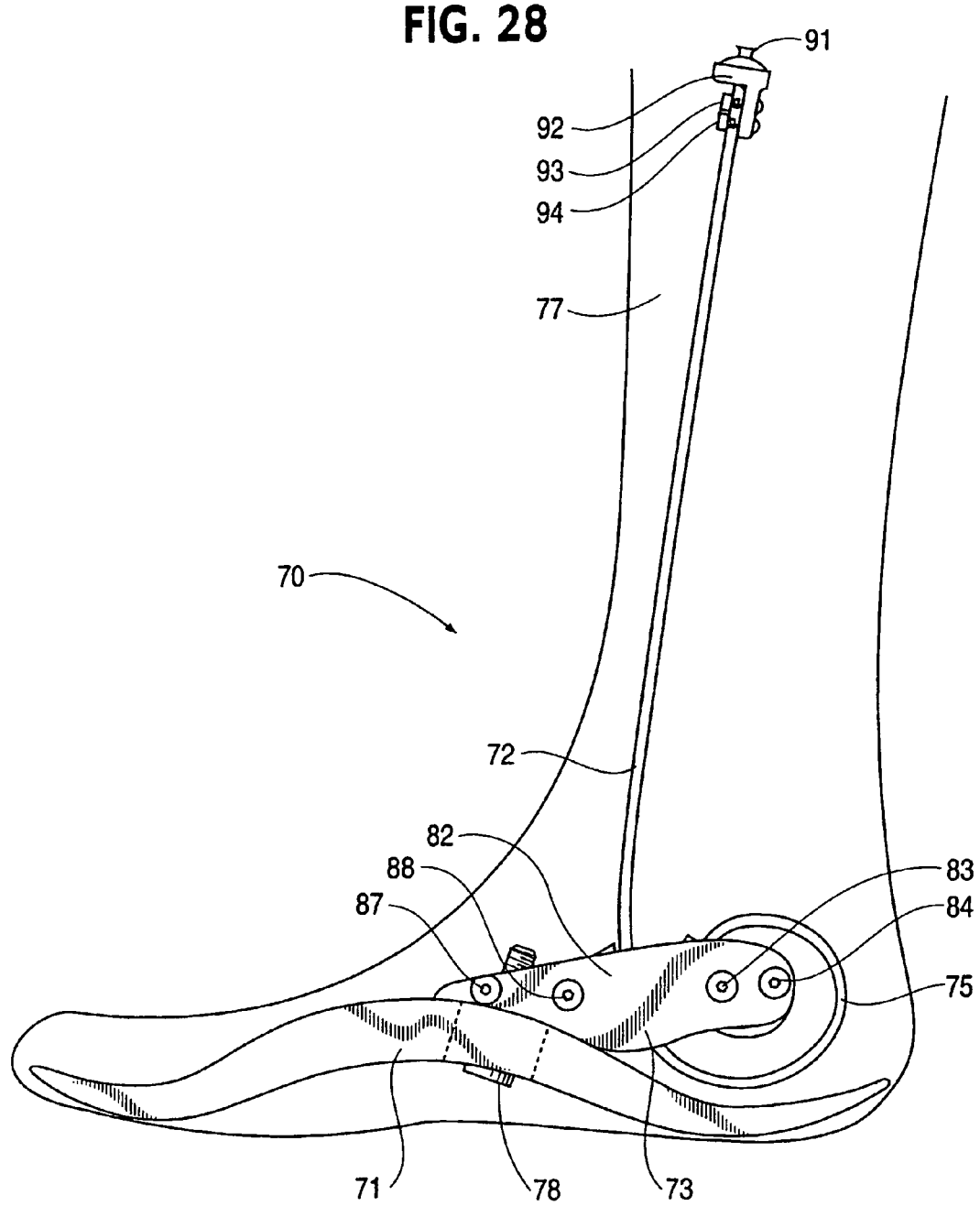
FIG. 28 is a side view of another embodiment of the prosthetic foot wherein the calf shank is utilized within a cosmetic covering.

The prosthetic foot 70 according to a further embodiment of the invention is depicted in FIGS. 28-31B. The prosthetic foot 70 comprises a foot keel 71, a calf shank 72 and a coupling element 73. The prosthetic foot 70 is similar to the prosthetic foot 53 in the embodiment of FIGS. 25-27, except that the calf shank 72 is formed with a downward, anteriorly facing convexly curved lower end 74 which is in the form of a spiral 75. The calf shank extends upward anteriorly from the spiral to an upstanding upper end thereof as seen in FIG. 28. The calf shank can be advantageously formed of metal, such as titanium, as noted above but other resilient materials could be used to form the semi-rigid, resilient calf shank.

The spiral shape at the lower end of the calf shank has a radius of curvature which progressively increases as the calf shank spirals outwardly from a radially inner end 76 thereof and as the calf shank extends upwardly from its lower, spiral end to its upper end, which may be curved in the longitudinal direction or straight. It has been found that this construction creates a prosthetic foot with an integrated ankle and calf shank with a variable radii response outcome similar to the parabola shaped calf shank of the invention, while at the same time allowing the coupling element 73 and the calf shank 72 to be more posterior on the foot keel 71. As a result, the calf shank and coupling element are more centrally concealed in the ankle and leg of a cosmetic covering 77, see FIG. 28.

The coupling element 73 is formed of plastic or metal alloy, and is adjustably fastened at its anterior end to the posterior of foot keel 71 by a threaded fastener 78 as shown in FIG. 30. The foot keel has a longitudinally extending opening 79 in an upwardly arched portion thereof which receives the fastener 78 to permit adjusting the alignment of the calf shank and foot keel with respect to one another in the longitudinal direction, e.g. along the line 30-30 in FIG. 29, in the manner explained above in connection with the other embodiments.

The posterior end of the coupling element includes a cross member 80 which is secured between two longitudinally extending plates 81 and 82 of the coupling element by metal screws 83 and 84 at each end of the cross member. The radially inner end 76 of the spiral 75 is secured to the cross member 80 of the coupling element by a threaded fastener 85 as depicted in FIG. 30. From its point of connection to the cross member, the calf shank spirals around the radially inner end 76 above the heel portion of the foot keel and extends upward anteriorly from the spiral through an opening 85 through the coupling element between plates 81 and 82 anterior of the cross member 80. A cross member 86 in the anterior end of coupling element 73 is secured between plates 81 and 82 by fasteners 87 and 88 at each end as seen in FIGS. 28 and 30. The fastener 78 is received in a threaded opening in cross member 86.

The posterior surface of the cross member 86 supports a wedge 89 formed of plastic or rubber, for example, which is adhesively bonded at 90 to the cross member. The wedge serves as a stop to limit dorsiflexion of the upwardly extending calf shank in gait. The size of the wedge can be selected, wider at 89' in FIG. 31A, or narrower at 89" in FIG. 31B, to permit adjustment of the desired amount of dorsiflexion. A plurality of the wedges could be used at once, one atop another and adhesively bonded to the coupling element for reducing the permitted dorsiflexion.

A prosthetic socket, not shown, attached to the amputee's lower leg stump can be connected to the upper end of the calf shank 72 via an adapter 92 secured to the upper end of the calf shank by fasteners 93 and 94 as shown in FIG. 28. The adapter has an inverted pyramid-shaped attachment fitting 91 connected to an attachment plate attached to an upper surface of the adapter. The pyramid fitting is received by a complementarily shaped socket-type fitting on the depending prosthetic socket for joining the prosthetic foot and prosthetic socket.

Figure 32:
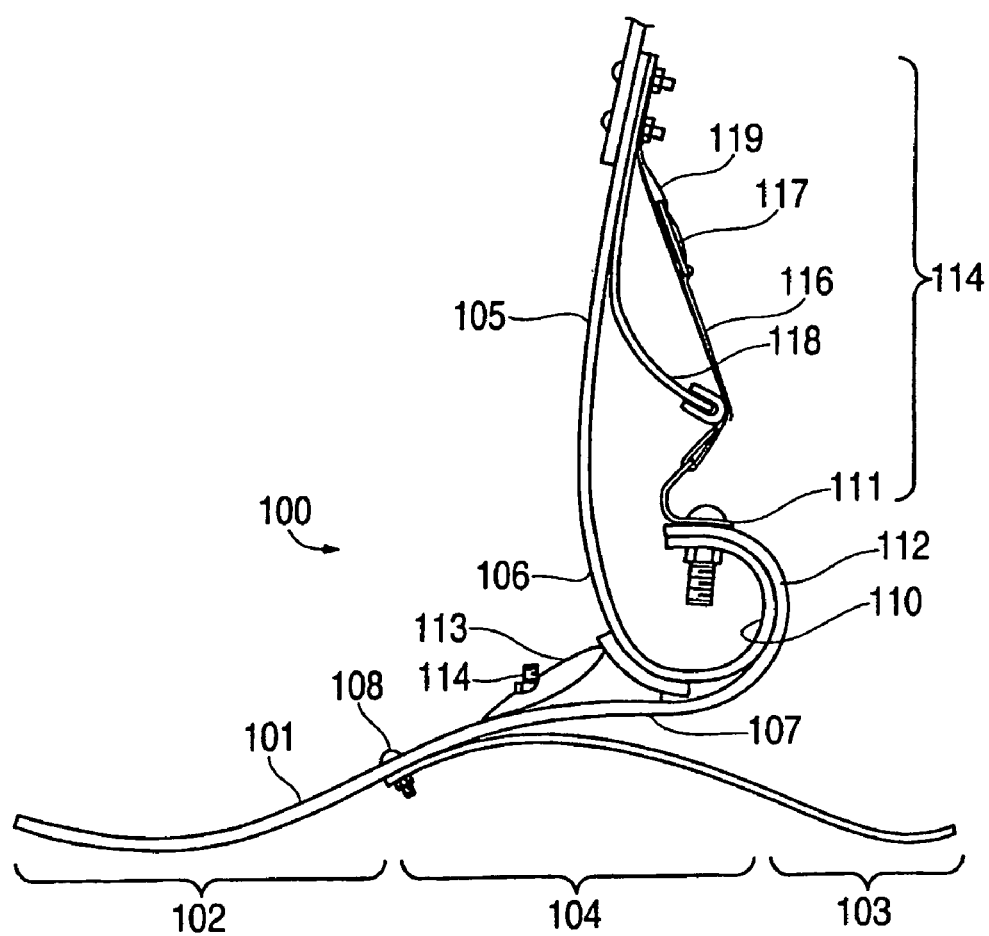
FIG. 32 is a side view of a further embodiment of the prosthetic foot wherein the lower end of the calf shank is reversely curved in the form of a spiral and housed within and supported by a coupling element monolithically formed with the forefoot portion of the foot keel.
Figure 33:
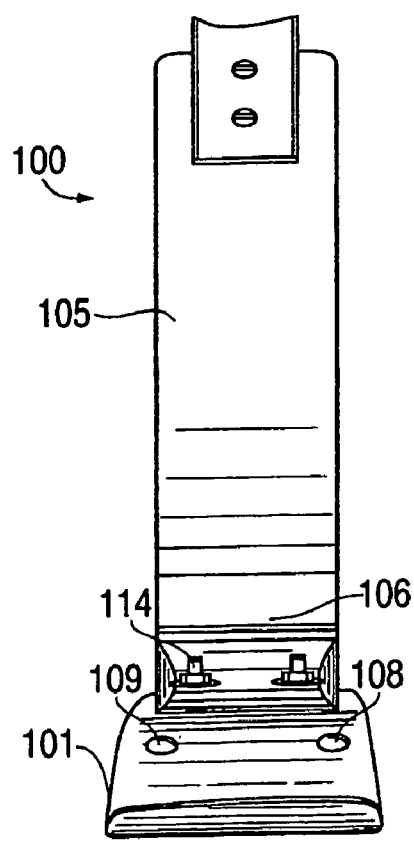
FIG. 33 is a front view of the prosthesis of FIG. 32.
Figure 34:
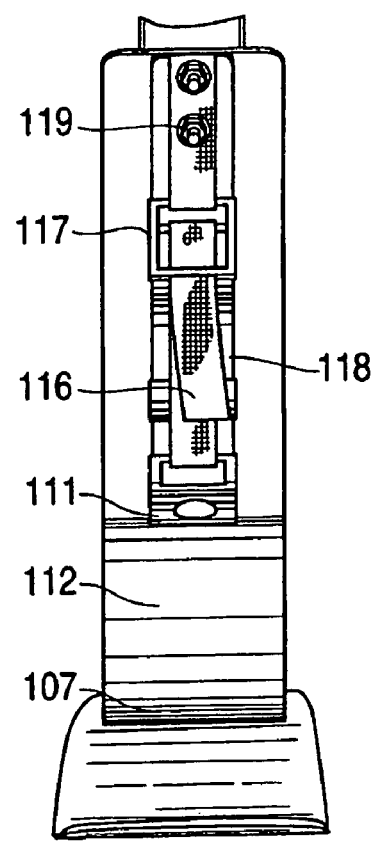
FIG. 34 is a rear view of the prosthesis of FIG. 32.

The prosthetic foot 100 of the embodiment of the invention of FIGS. 32-34 comprises a longitudinally extending foot keel 101 having a forefoot portion 102 at one end, a hindfoot portion 103 at an opposite end and a midfoot portion 104 extending between the forefoot and hindfoot portions. An upstanding calf shank 105 is secured to the foot keel at a lower end of the calf shank to form an ankle joint of the prosthetic foot and extends upward from the foot keel by way of an anterior facing convexly curved portion 106 of the calf shank. The calf shank is secured to the foot keel by way of a coupling element 107 which is monolithically formed with the forefoot portion 102 of the foot keel. The coupling element extends posteriorly from the forefoot portion as a cantilever over the midfoot portion 104 and part of the hindfoot portion 103. The hindfoot portion and the midfoot portion of the foot keel are monolithically formed and connected to the monolithically formed forefoot portion and coupling element by fasteners 108 and 109.

The lower end of the calf shank 105 is reversely curved in the form of a spiral 110. A radially inner end of the spiral 110 is fastened to the coupling element by a connector 111 in the form of a threaded bolt and nut extending through facing openings in the calf shank and the coupling element. The coupling element posterior portion 112 is reversely curved to house the spiral lower end of the calf shank, which is supported at the upper end of the curved portion 112 by the connector 111.

A stop 113 connected to the coupling element of the foot keel by fasteners 114 and 115, limits dorsiflexion of the calf shank. A cosmetic covering anterior of the calf shank in the shape of a human foot and lower leg is optionally located over the foot keel 101 and at least the lower end of the calf shank 105 with the calf shank extending upwardly from the foot keel within the lower leg covering in the manner illustrated and described in connection with the embodiment of FIG. 28.

The prosthetic foot 100 of the embodiment of FIGS. 32-34 has increased spring efficiency of the foot keel. Increasing the length of the resilient foot keel from the toe region to the connection to the lower end of the calf shank by the use of the monolithically formed forefoot portion and coupling element results in a significant spring rate gain. When the toe region of the foot keel is loaded in the late midstance phase of gait, the downward facing concavity of the cantilevered coupling element expands and the reversely curved, anterior facing concavity at the posterior end of the coupling element is compressed, each of these resilient flexures of the coupling element of the foot keel stores energy for subsequent release, during unloading, in a direction which aids the forward propulsion of the limb in gait. The ankle formed by the lower end of the calf shank in the prosthesis replicates human ankle joint function, the prosthesis helping to conserve forward momentum and inertia. The configuration of the foot keel in the embodiment is not limited to that shown but could be any of the foot keel configurations shown previously including those having a high-low gear or a high gear only, having one or more expansion joints, or being formed with plural longitudinal sections, for example. Similarly, the calf shank of the embodiment could have its upper end, e.g. above the ankle and the anterior facing convexly curved portion extending upward from the foot keel, configured differently as for example with a configuration in any of the other embodiments disclosed herein. The upper end of the calf shank can be connected to a socket on the lower limb of a person for use by means of an adapter, for example that in FIG. 3, FIG. 27 or FIG. 28, or other known adapter.

The prosthetic foot 100 in FIGS. 32-34 further includes a posterior calf device 114 to store additional energy with anterior motion of the upper end of the calf shank in gait. That is, in the active propulsion phase of gait force loading of the resilient prosthesis expands the sagittal plane concavity of the shank 105 formed by the anterior facing convexly curved portion 106 of the calf shank which results in anterior movement of the upper end of the calf shank relative to the lower end of the calf shank and the foot keel. A flexible elongated member 116, preferably in the form of a strap, of the device 114 is connected to an upper portion of the calf shank by fasteners 119 and to a lower portion of the prosthetic foot, namely to coupling element 107 and lower end 110 of the shank by connector 111 as discussed above. The length of the flexible strap, which can be elastic and/or non-elastic, is tensioned in gait and can be fixed in length or adjusted by use of a slide adjustment 117 between overlapping lengths of the strap.

A curvilinear spring 118 is adjustably supported at its base on the upper end of the calf shank, for example between the calf shank and an adapter, not shown, secured to the calf shank, with fasteners 119. The lower, free end of the spring is positioned to interact with the flexible strap. When the strap is tensioned the spring changes the direction of the longitudinal extent of the strap. Anterior movement of the upper end of the calf shank in gait tensions/further tensions (if the strap is initially preloaded in tension) the strap and loads/further loads the spring to store energy in force loading of the prosthetic foot in gait. This stored energy is returned by the spring in force unloading of the prosthetic foot to increase the kinetic power generated for propulsive force by the prosthetic foot in gait.

When the strap 116 is shortened using the slide adjustment 117 to initially preload the strap in tension prior to use of the prosthetic foot, the strap tension serves to assist posterior movement of the upper end of the resilient shank as well as control anterior movement of the calf shank during use of the prosthesis. Assisting the posterior movement can be helpful in attaining a rapid foot flat response of the prosthetic foot at heel strike in the initial stance phase of gait akin to that which occurs in a human foot and ankle in gait at heel strike where plantarflexion of the foot occurs.

The assisting posterior movement and the controlling anterior movement of the upper end of the resilient calf shank during use of the prosthesis using the posterior calf device 114 are each effective to change the ankle torque ratio of the prosthetic foot in gait by affecting a change in the sagittal plane flexure characteristic for longitudinal movement of the upper end of the calf shank in response to force loading and unloading during a person's use of the prosthetic foot. The natural physiologic ankle torque ratio in the human foot in gait, defined as the quotient of the peak dorsiflexion ankle torque that occurs in the late terminal stance of gait divided by the plantar flexion ankle torque created in the initial foot flat loading response after heel strike in gait has been reported as 11.33 to 1. An aim of changing the sagittal plane flexure characteristic for longitudinal movement of the upper end of the calf shank using the posterior calf device 114 is to increase the ankle torque ratio of the prosthesis to mimic that which occurs in the human foot in gait. This is important for achieving proper gait with the prosthesis and, for a person with one natural foot and one prosthetic foot, for achieving symmetry in gait. Preferably, through controlling anterior movement and possibly assisting posterior movement using the posterior calf device 114, the ankle torque ratio of the prosthesis is increased so that the peak dorsiflexion ankle torque which occurs in the prosthesis is an order of magnitude greater than the plantar flexion ankle torque therein. More preferably, the ankle torque ratio is increased to a value of about 11 to 1, to compare with the reported natural ankle torque ratio of 11.33 to 1.

A further purpose of the posterior calf device is to improve the efficiency of the prosthetic foot in gait by storing additional elastic energy in the spring 118 of the device during force loading of the prosthesis and to return the stored elastic energy during force unloading to increase the kinetic power generated for propulsive force by the prosthetic foot in gait. The device 114 may be considered to serve the purpose in the prosthetic foot that the human calf musculature serves in the human foot, ankle and calf in gait, namely efficiently generating propulsive force on the person's body in gait utilizing the development of potential energy in the body during force loading of the foot and the conversion of that potential energy into kinetic energy for propulsive force during force unloading of the foot. Approaching or even exceeding the efficiencies of the human foot in the prosthetic foot of the invention with the posterior calf device is important for restoring "normal function" to an amputee for example. The control of anterior movement of the upper end of the calf shank 105 by the posterior calf device 114 is effective to limit the range of anterior movement of the upper end of the calf shank. The foot keel in the prosthetic foot 100 by the expansion of its resilient longitudinal arch in the coupling element 107 and the compression of reversely curved portion 112 of the coupling element also contributes to storing energy during force loading in gait as discussed above. This potential energy is returned as kinetic power for generating propulsive during force unloading in gait.

Figure 35:
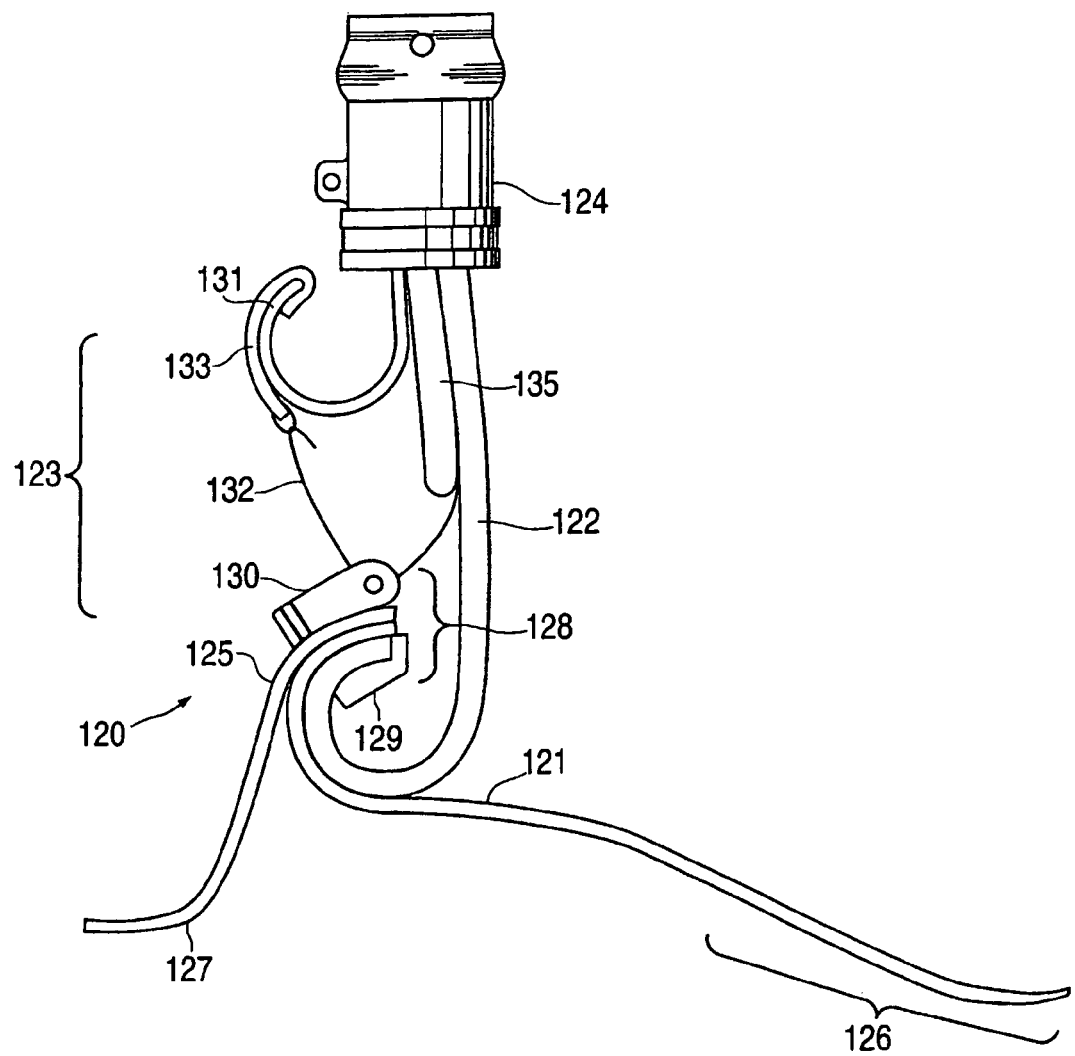
FIG. 35 is a side view of another embodiment of the prosthesis wherein a posterior component of the foot keel is joined to the reversely curved upper end of the coupling element which is monolithically formed with the forefoot portion of the foot keel.
Figure 39:
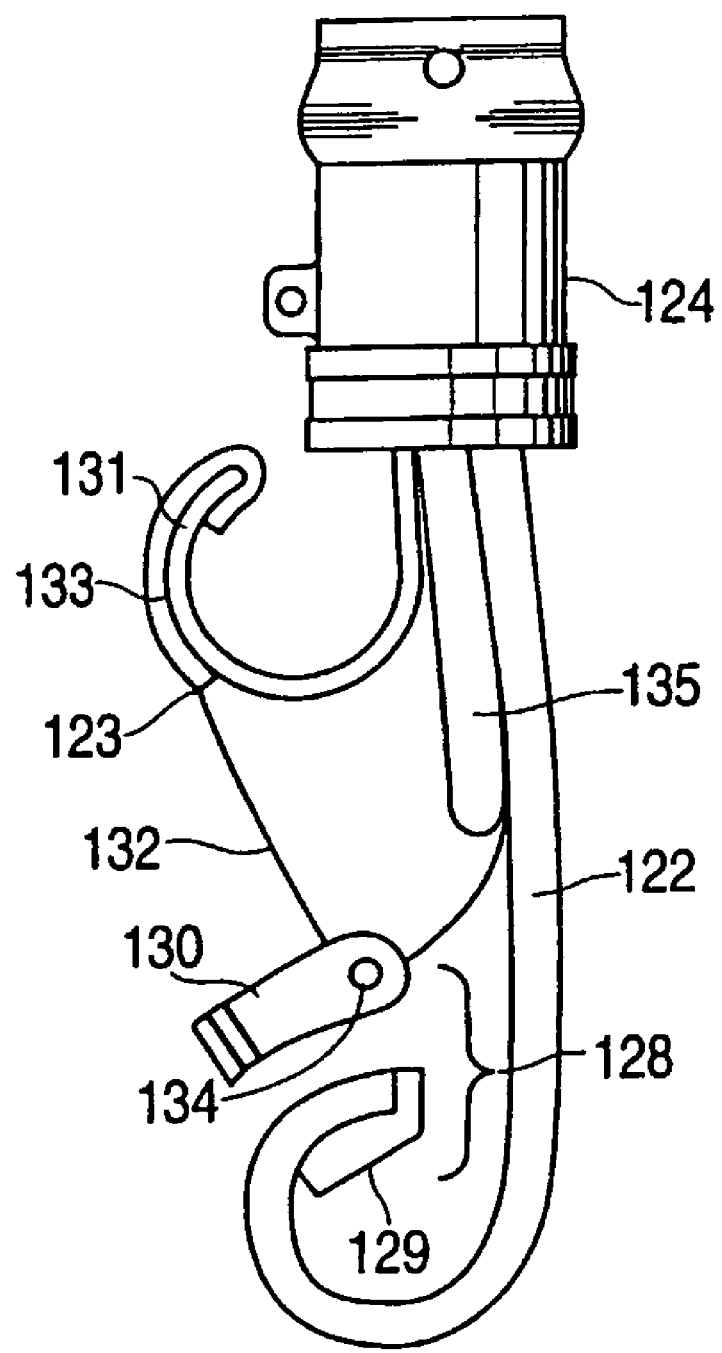
FIG. 39 is a side view of the calf shank and posterior calf device of the embodiments of FIGS. 35-38 shown disassembled from the foot keel and its coupling element.

The prosthesis 120 in FIG. 35 comprises a foot keel 121, a calf shank 122 and a posterior calf device 123. An adapter 124 is connected by suitable fasteners, not shown, to the upper end of the calf shank for securing the prosthesis to a socket on the lower limb of a person for use. Like the embodiment of FIGS. 32-34, a coupling element 125 of the prosthesis is monolithically formed with a forefoot portion 126 of the foot keel. A hindfoot portion 127 of the foot keel is joined to the upper end of the reversely curved portion of the coupling element by a fastener arrangement 128, shown disassembled in FIG. 39 prior to connection to the coupling element and calf shank.

The fastener arrangement includes a radially inner component 129 against the radially inner end of the reversely curved spiral of the lower end of the calf shank, and a radially outer component 130 against the upper end of the hindfoot portion 127. A mechanical fastener, not shown, such as a through bolt and nut, extends through aligned openings in the components 129 and 130 and the complementarily curved portions of the hindfoot portion, coupling element and calf shank lower end which are sandwiched between and joined to one another by the fastening arrangement.

The posterior calf device 123 on the prosthetic foot 120 includes a coiled spring 131 supported at its one end at the upper end of the calf shank for movement therewith. A second, free end of the coiled spring has one end of a flexible elongated member, strap 132, secured thereto by a metal clip 133. The clip is connected at its one end to a first end of the strap and at its other end is hooked over in clamping engagement with the free end of the coiled spring as depicted in FIG. 35. An intermediate portion of the flexible strap 132 extends down to the foot keel and lower end of the calf shank where it extends about a return 134 in the form of a cylindrical pin 135 mounted on the component 130 of the fastener arrangement 128. To minimize sliding resistance of the strap against the pin, the pin 134 may be rotatably mounted in the component 130. The second end of the strap is clampingly retained at the upper end of the calf shank between the posterior surface of the shank and a complementarily shaped spring retainer member 135 which extends part way down the length of the shank. The upper end of the member 135 is secured between the upper end of the coiled spring and the upper end of the shank by suitable fasteners, not shown. The length of the flexible strap, which can be elastic and/or non-elastic, is tensioned in gait. This length is fixed, or it can be adjusted by use of a slide adjustment, not shown, between overlapping lengths of the strap adjacent the connection to the metal clip 133, for example.

Anterior movement of the upper end of the shank relative to the foot keel and lower end of the shank in gait is yieldably resisted by expansion of the coiled spring 131 and posterior flexing of the lower end of the retainer member 135 to store energy during force loading of the prosthesis in the late mid-stance phase of gait, which stored energy is released during force unloading thereby contributing to ankle power generation in the prosthesis and improving efficiency. The coiled spring 131 is formed of spring steel in the embodiment but other metal alloys or non-metals such as plastic could be employed. The spring retainer member 135 is formed of carbon fiber encapsulated in epoxy resin in the embodiment but other materials, including a metal alloy, and plastic could be used. The flexible strap 132, like the strap 116 in FIGS. 32-34, is made of a woven Kevlar (DuPont) material having a width of $5/8$ inch and a thickness of $1/16$ inch but other materials and dimensions could be employed as will be apparent to the skilled artisan. The first end of the strap 132 extends through an opening in the end of the metal clip 133 and is doubled back on the strap where it is adjustably retained by a slide adjustment or other fastener.

Figure 36:
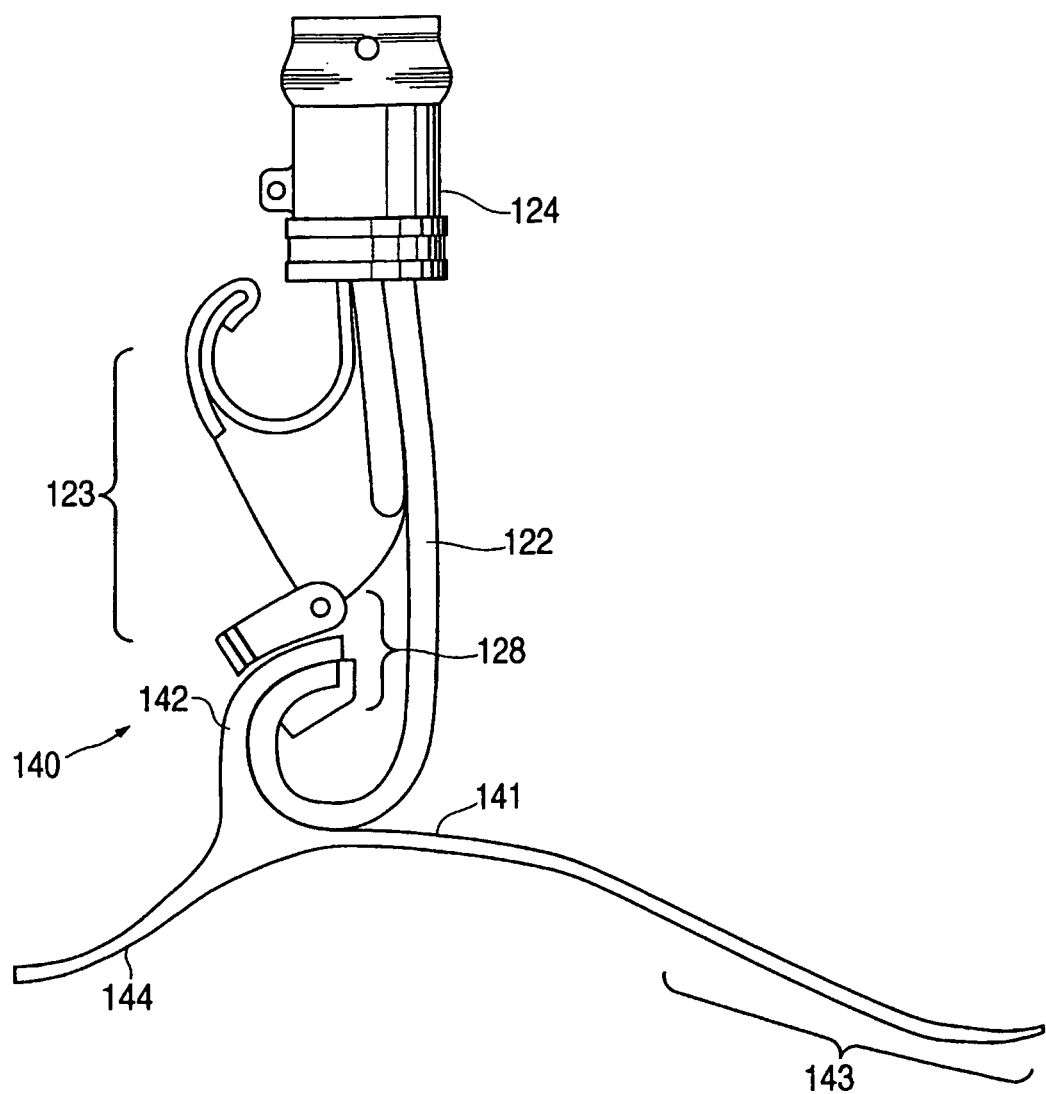
FIG. 36 is a side view of another form of the invention wherein the coupling element is monolithically formed with the foot keel.

The prosthesis 140 in the embodiment of FIG. 36 employs the calf shank 122 and posterior calf device 123 used with the prosthesis 120 of FIG. 35. The foot keel 141 of the prosthetic foot 140 includes a reversely curved coupling element 142 connected to the lower end of the calf shank by fastener arrangement 128 for housing and supporting the spiral lower end of the calf shank. In this form of the invention the coupling element is monolithically formed with both the forefoot portion 143 and the hindfoot portion 144 of the foot keel.

Figure 37:
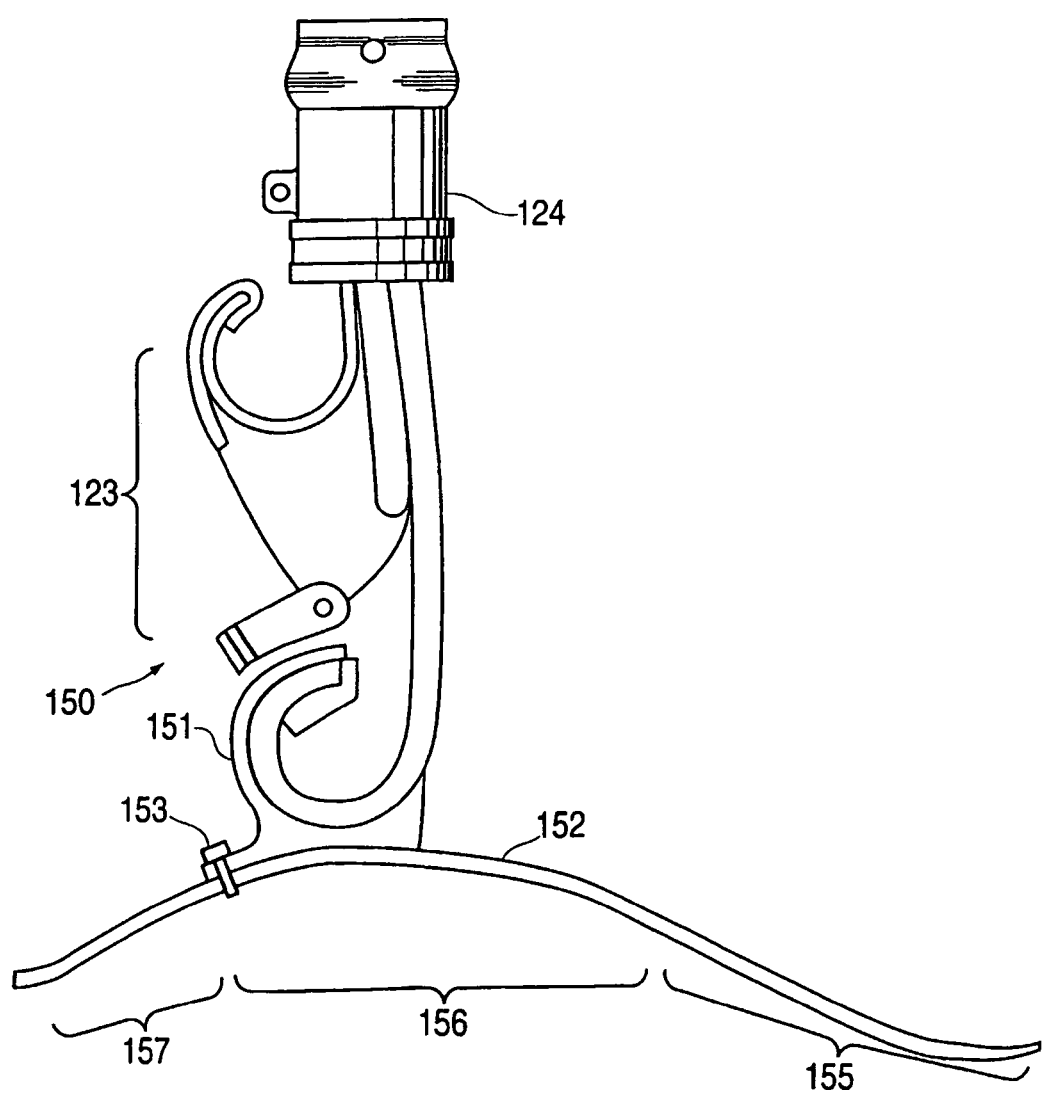
FIG. 37 is a side view of a still further variation of the prosthesis of the invention wherein the coupling element is joined at a posterior end thereof to the foot keel by a fastener.
Figure 38:
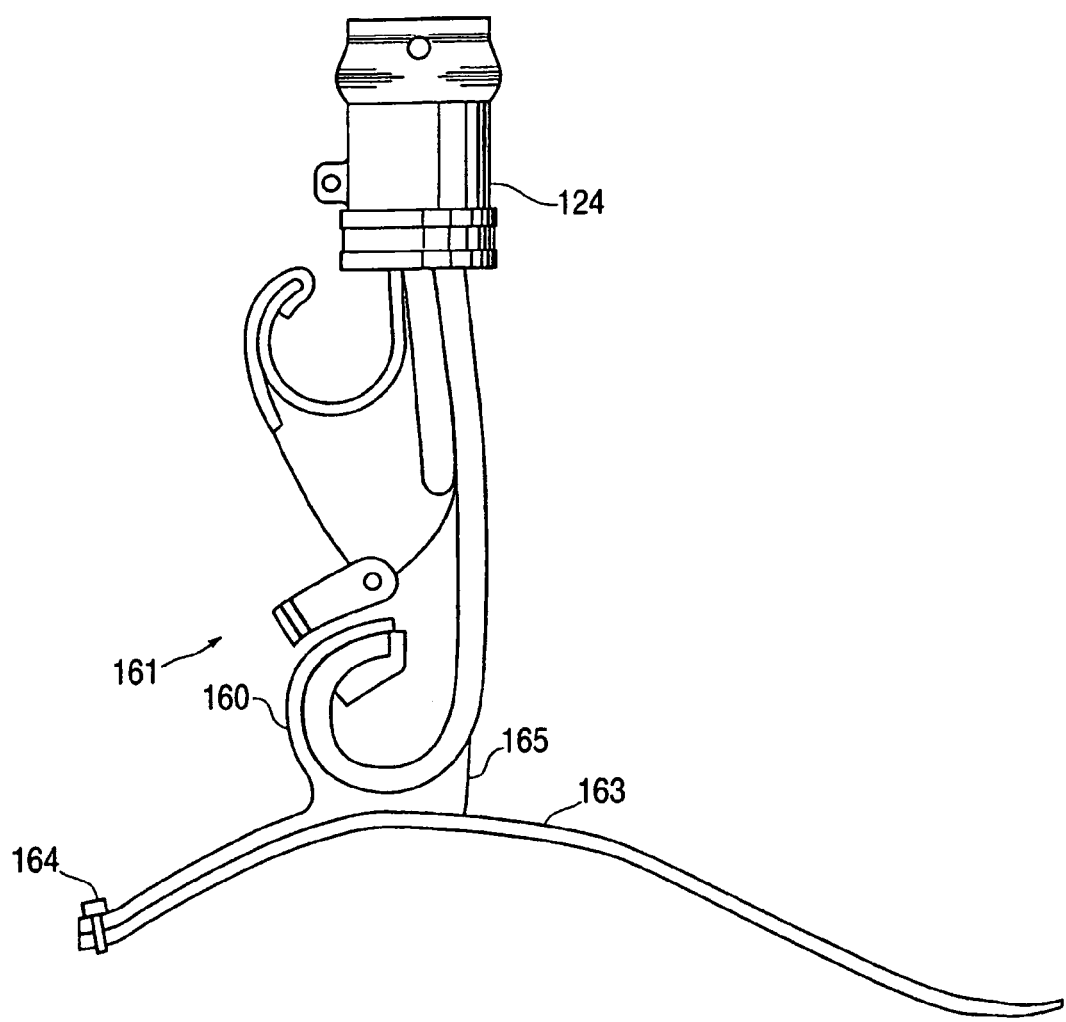
FIG. 38 is a side view of another embodiment of the prosthesis showing the coupling element joined to the foot keel at the posterior end of the foot keel.

The prosthetic foot 150 of the embodiment of FIG. 37 is like that in FIGS. 35 and 36 except that the coupling element 151 is formed as a separate element which is secured at its posterior end by a fastener 153 to the foot keel 152 forming the forefoot, midfoot and hindfoot portions 155, 156 and 157 of the foot keel. The area of the connection at fastener 153 is posterior the connection of the calf shank and the coupling element for increasing the active length of the foot keel and its spring rate in the late mid-stance phase of gait. This effect is still greater in the embodiment of FIG. 38 where the coupling element 160 of the prosthesis 161 extends to the posterior end of the foot keel 163 where it is connected to the foot keel by fastener 164. The fastener can be a mechanical fastener such as a bolt and nut or other fastener including a composite of wrapped carbon fiber and epoxy resin or a composite of a wrapped aromatic polyamide fiber such as Kevlar by DuPont and epoxy resin. The lower anterior end 165 of the coupling element is extended to serve as a stop for the anterior movement of the calf shank in dorsiflexion. Alternatively, a separate stop as provided at 113 in the embodiment of FIGS. 32-34 could be provided. Either type of stop could also be used in the embodiments of FIGS. 35 and 36.

Figure 40:
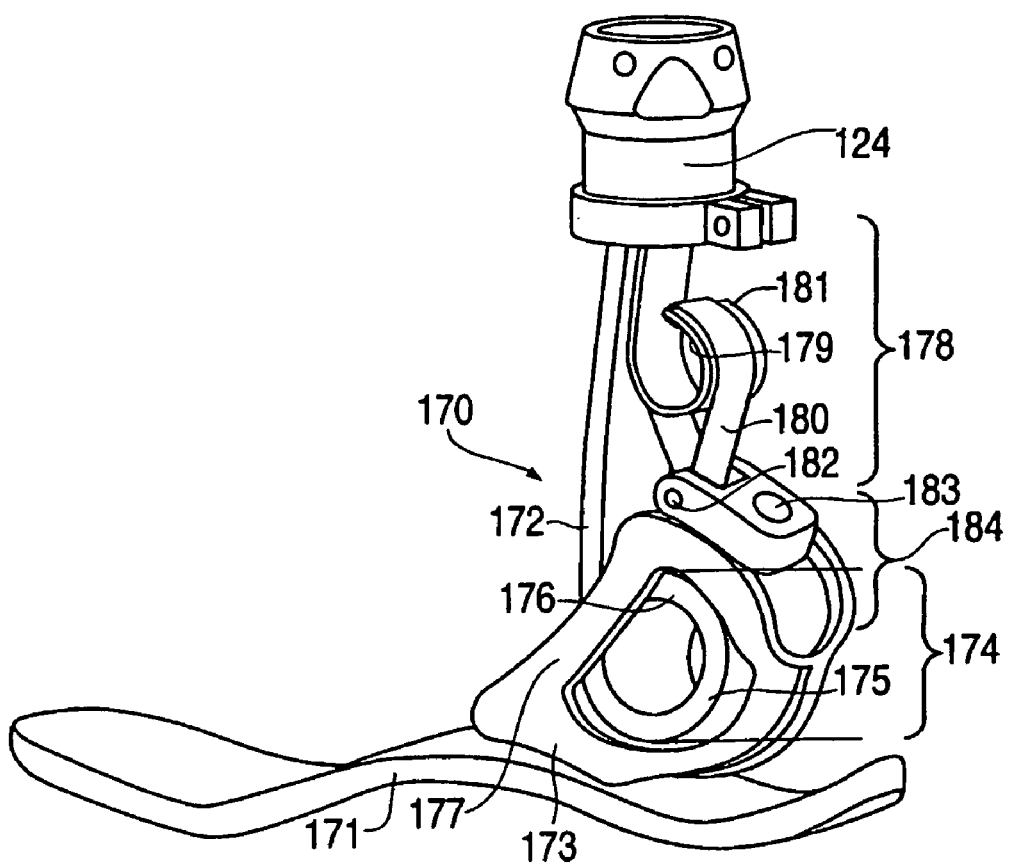
FIG. 40 is a perspective from the left side and to the rear of a prosthetic foot of an additional embodiment of the invention combining features of several other embodiments.

The prosthetic foot 170 in FIG. 40 is similar to the prosthetic foot in the embodiment of FIGS. 28-31B. The prosthesis 170 includes a foot keel 171, a calf shank 172 and a coupling element 173. The shank 172 is formed with a downward, anterior facing convexly curved lower end 174 which is reversely curved in the form of a spiral 175. The calf shank extends upward from the spiral to an upstanding upper end thereof, which may be curved in the longitudinal direction or straight.

The spiral shape at the lower end of the calf shank has a radius of curvature which progressively increases as the calf shank spirals outwardly from a radially inner, upper end 176 where it is fastened to the coupling element by a connector, not shown, in the form of a threaded bolt and nut extending through facing openings in the calf shank and coupling element as in the embodiments of FIGS. 32-38.

The coupling element 173 serves as a housing for the spiral 175 and is adjustably fastened to the foot keel 171 by a threaded fastener as in FIG. 30. The foot keel has a longitudinally extending opening in an upwardly arched portion thereof which receives the fastener to permit adjusting the alignment of the calf shank and foot keel with respect to one another in the longitudinal direction as explained in connection with the other embodiments. Instead of longitudinally extending plates 81 and 82 as in FIGS. 28-30, the coupling element 173 is formed with open sides and an anterior facing opening bounded laterally by laterally spaced, anterior side edges 177 of the coupling element. The calf shank extends upwardly through the anterior facing opening as in the embodiment of FIGS. 28-30. A stop, not shown, can be provided as in FIGS. 28-30 to limit dorsiflexion of the calf shank in gait.

An adapter 124, like that in the embodiments of FIGS. 35-39 is connected by suitable fasteners, not shown, to the upper end of the calf shank for securing the prosthesis to a socket on the lower limb of a person for use. A posterior calf device 178 on the prosthetic foot 170 is like device 123 in FIG. 35 and includes a coiled spring 179 supported at its one end at the upper end of the calf shank for movement therewith. A second, free end of the coiled spring has one end of a flexible elongated member, strap 180, secured thereto by a metal clip 181. The clip is connected at its one end to a first end of the strap and at its other end is hooked over in clamping engagement with the free end of the coiled spring as in the posterior calf device in FIG. 35. An intermediate portion of the flexible strap 180 extends down to the foot keel and lower end of the calf shank where it extends about a return 182 in the form of a cylindrical pin mounted on component 183 of the fastener arrangement 184 joining the coupling element and lower end of the calf shank. The pin 182 may be rotatably mounted in the component 183 to minimize sliding resistance. The second end of the strap is clampingly retained at the upper end of the calf shank between the shank and the coiled spring. The flexible strap can be fixed in length or adjustable in length by use of a slide adjustment, not shown, as in the embodiment of FIG. 35. The device 178 serves to store energy during force of the prosthesis in the late midstance phase of gait, which stored energy is released during force unloading thereby contributing to sagittal plane ankle power generation as discussed with respect to the embodiment of FIG. 35.

One difference between the prosthesis 170 in FIG. 40 and prosthesis 70 in FIGS. 28-30 is that the ankle of the prosthesis 170 is higher above the ground than the ankle in prosthesis 70. Note the lower end of the reversely curved, spiral ankle joint 174 in FIG. 40 is above the upwardly arched midportion of the foot keel 171 in FIG. 40 because of the upwardly and posteriorly extending configuration of the coupling element 173 whereas the lower end 75 of the spiral 74 in prosthesis 70 of FIGS. 28-30 is lower than the height of the upwardly arched midportion of the foot keel. It has been recognized that the height of this ankle area above the ground affects the ankle's sagittal plane angular change which occurs in the stance phase of gait. A higher placement of the ankle area will increase the angular change while a lower placement of the ankle will decrease the angular change. Therefore, the higher placement of the ankle as in FIG. 40 has greater angular velocity potential for the same amount of angular change that occurs at the proximal end of the shank. This increase in angular velocity is quite significant; for example, an ankle height of two inches has 35% less angular change than an ankle height of three and one-half inches. The ankle height in the prosthesis of the invention is determined by a number of factors including the size and configuration of the coupling element, the longitudinal arch height, the length of the forefoot, midfoot and hindfoot portions of the foot keel, etc. as will be apparent to the skilled artisan.

This concludes the description of the example embodiments. Although the present invention has been described with reference to a number of illustrative embodiments, it should be understood that numerous other modifications and embodiments can be devised by those skilled in the art that will fall within the spirit and scope of the principles of this invention. For example, the lower end of the calf shank in the prosthetic foot of the invention is not limited to a parabola shape or a spiral shape but can be hyperbolic or otherwise downward convexly, curvilinearly configured to produce the desired motion outcomes of the foot when connected to the foot keel to form the ankle joint area of the foot. The posterior calf device is not limited in its use of a strap as the flexible elongated member as other members such as a flexible wire cable could be used. Likewise, the configuration of a spring in the device could be different than those shown. For example, a resilient tube of metal or plastic extending transversely to the longitudinal extent of the prosthesis could be interposed between the elongated member and the upper portion of the shank for storing and releasing energy. The features of the various embodiments including the materials for construction could also be used with one another. More particularly, reasonable variations and modifications are possible in the component parts and/or arrangements of the subject combination arrangement within the scope of the foregoing disclosure, the drawings, and the appended claims without departing from the spirit of the invention. In addition to variations and modifications in the component parts and/or arrangements, alternative uses will also be apparent to those skilled in the art.

We claim:

1. A prosthetic foot comprising:
    a longitudinally extending foot keel having a forefoot portion at one end, a hindfoot portion at an opposite end and an upwardly arched midfoot portion extending between said forefoot and hindfoot portions;
    an ankle secured to the foot keel;
    an upstanding calf shank extending upward from the ankle;
    wherein the ankle and calf shank are monolithically formed as a resilient member having a reversely curved lower end secured to the foot keel to form the ankle and extending upward from the foot keel by way of an anterior facing convexly curved portion of the member, and
    a posterior calf device on the prosthesis to store enemy during force loading of the prosthesis and return the stored energy during force unloading to increase the kinetic power generated for propulsive force by the prosthesis in gait, wherein the posterior calf device includes at least one elongated member extending between the upper portion of the calf shank and a lower portion of the prosthetic foot, and at least one spring which is resiliently biased by the at least one elongated member in response to anterior movement of the upper end of the shank for storing energy,
    wherein the resilient member is secured to the foot keel by way of a coupling element which is monolithically formed with the forefoot portion of the foot keel, wherein the hindfoot portion and the midfoot portion of the foot keel are monolithically formed and connected to the monolithically formed forefoot portion and coupling element and wherein the coupling element extends posteriorly from the forefoot portion as a cantilever over the midfoot portion and part of the hindfoot portion of the foot keel,
    wherein the reversely curved lower end of the resilient member is in the form of a posteriorly-oriented spiral, and wherein the coupling element forms an anterior facing concavity within which the reversely curved lower end of the resilient member is housed.

2. The prosthetic foot according to claim 1, wherein a radially inner end of the spiral of the resilient member is fastened to the coupling element.

3. The prosthetic foot according to claim 1, wherein the coupling element includes a stop to limit dorsiflexion of the resilient member.

4. The prosthetic foot according to claim 1, further comprising a cosmetic covering in the shape of a human foot and lower leg, the cosmetic covering being located over the foot keel, ankle and at least the lower end of the calf shank with the calf shank extending upward from the ankle within the lower leg covering.

5. The prosthetic foot according to claim 1, wherein the at least one spring includes a coiled spring with a free end connected to the elongated member, the coiled spring being resiliently expanded in response to anterior movement of the upper end of the shank in gait for storing energy.

6. The system-prosthetic foot according to claim 1, wherein the coupling element is configured to position a lower end of the ankle at a height above the ground higher than the upwardly arched midfoot portion of the foot keel.

* * * * *